United States Patent
Abbott et al.

(10) Patent No.: US 12,281,171 B2
(45) Date of Patent: Apr. 22, 2025

(54) PERIOSTIN ANTIBODIES AND METHODS OF USING THE SAME

(71) Applicants: BioVentures, LLC, Little Rock, AR (US); SRI International, Menlo Park, CA (US)

(72) Inventors: Karen Abbott, Little Rock, AR (US); Nathalie Scholler, Playa Del Rey, CA (US)

(73) Assignees: Bio Ventures, LLC, Little Rock, AR (US); SRI International, Menlo Park, CA (US)

(*) Notice: Subject to any disclaimer, the term of this patent is extended or adjusted under 35 U.S.C. 154(b) by 1187 days.

(21) Appl. No.: 16/982,476

(22) PCT Filed: Mar. 19, 2019

(86) PCT No.: PCT/US2019/023020
§ 371 (c)(1),
(2) Date: Sep. 18, 2020

(87) PCT Pub. No.: WO2019/183131
PCT Pub. Date: Sep. 26, 2019

(65) Prior Publication Data
US 2021/0017288 A1 Jan. 21, 2021

Related U.S. Application Data

(60) Provisional application No. 62/727,915, filed on Sep. 6, 2018, provisional application No. 62/644,681, filed on Mar. 19, 2018.

(51) Int. Cl.
*C07K 16/30* (2006.01)
*A61K 39/00* (2006.01)
*A61K 49/00* (2006.01)
*A61K 49/16* (2006.01)
*G01N 33/574* (2006.01)

(52) U.S. Cl.
CPC .......... *C07K 16/30* (2013.01); *A61K 49/0058* (2013.01); *A61K 49/16* (2013.01); *C07K 16/3023* (2013.01); *G01N 33/57492* (2013.01); *A61K 2039/505* (2013.01); *C07K 2317/56* (2013.01); *C07K 2317/565* (2013.01); *C07K 2317/622* (2013.01); *C07K 2317/732* (2013.01)

(58) Field of Classification Search
CPC ................ C07K 16/30; C07K 16/3023; A61K 49/0058; A61K 49/16
See application file for complete search history.

(56) References Cited

U.S. PATENT DOCUMENTS

| | | | |
|---|---|---|---|
| 5,122,368 A | 6/1992 | Greenfield | |
| 5,622,929 A | 4/1997 | Willner | |
| 5,824,805 A | 10/1998 | King | |
| 6,214,345 B1 | 4/2001 | Firestone | |
| 7,223,837 B2 | 5/2007 | De Groot | |
| 7,521,056 B2 | 4/2009 | Chang | |
| 7,527,787 B2 | 5/2009 | Chang | |
| 7,534,866 B2 | 5/2009 | Chang | |
| 7,550,143 B2 | 6/2009 | Chang | |
| 7,666,400 B2 | 2/2010 | Chang | |
| 7,705,045 B2 | 4/2010 | De Groot | |
| 7,829,531 B2 | 11/2010 | Senter | |
| 7,837,980 B2 | 11/2010 | Alley | |
| 7,847,105 B2 | 12/2010 | Gangwar | |
| 7,851,437 B2 | 12/2010 | Senter | |
| 7,968,586 B2 | 6/2011 | Gangwar | |
| 7,989,434 B2 | 8/2011 | Feng | |
| 8,034,787 B2 | 10/2011 | DuBois | |
| 8,034,959 B2 | 10/2011 | Ng | |
| 8,039,273 B2 | 10/2011 | Jeffrey | |
| 8,067,546 B2 | 11/2011 | McDonagh | |
| 2005/0238649 A1 | 10/2005 | Doronina | |
| 2006/0024308 A1 | 2/2006 | Crea | |
| 2006/0024317 A1 | 2/2006 | Boyd | |
| 2006/0074008 A1 | 4/2006 | Senter | |
| 2010/0266613 A1* | 10/2010 | Harding | A61P 37/06 435/69.6 |
| 2011/0033875 A1 | 2/2011 | Pierce et al. | |
| 2012/0156194 A1 | 6/2012 | Arron et al. | |
| 2012/0258108 A1* | 10/2012 | Ghayur | A61P 13/10 435/258.1 |
| 2014/0154710 A1 | 6/2014 | Pierce | |

FOREIGN PATENT DOCUMENTS

| | | |
|---|---|---|
| EP | 0453082 A1 | 10/1991 |
| EP | 2757376 | 11/2014 |
| WO | 2002083180 A1 | 10/2002 |
| WO | 2003016471 A2 | 2/2003 |
| WO | 2004010957 A2 | 2/2004 |
| WO | 2004043493 A1 | 5/2004 |
| WO | 2005112919 A2 | 12/2005 |
| WO | 2006110476 A2 | 10/2006 |

(Continued)

OTHER PUBLICATIONS

Almagro & Fransson, Humanization of antibodies, Frontiers in Bioscience 2008; 13: 1619-33 (Year: 2008).*

(Continued)

*Primary Examiner* — Peter J Reddig
*Assistant Examiner* — Cheng Lu
(74) *Attorney, Agent, or Firm* — Quarles & Brady, LLP

(57) ABSTRACT

The present inventors have developed antigen-binding reagents and antigen-binding conjugates that recognize a cancer-specific glycan (carbohydrate) modification on the human Periostin protein. Various in vitro and in vivo diagnostic and/or therapeutic methods using these compositions are also disclosed herein specifically for treating cancers that have amplification of the Mgat3 gene.

13 Claims, 18 Drawing Sheets

Specification includes a Sequence Listing.

(56) References Cited

FOREIGN PATENT DOCUMENTS

| WO | 2007018431 A2 | 2/2007 |
|---|---|---|
| WO | 2007059404 A2 | 5/2007 |
| WO | 2007089149 A2 | 8/2007 |
| WO | 2009017394 A2 | 2/2009 |
| WO | 2010062171 A2 | 6/2010 |
| WO | 2015120171 A1 | 8/2015 |
| WO | 2016016265 A1 | 2/2016 |
| WO | 2016057890 A1 | 4/2016 |
| WO | 2017060482 A1 | 4/2017 |

OTHER PUBLICATIONS

Rudikoff et al., Single amino acid substitution altering antigen-binding specificity, PNAS, USA, 1982, 79: 1979-1983 (Year: 1982).*
Riemer et al., Matching of trastuzumab (Herceptin®) epitope mimics onto the surface of Her-2/neu—a new method of epitope definition, Mol Immunol, 2005 42(9): 1121-1124 (Year: 2005).*
Zhu, M. et al., "Neutralizing monoclonal antibody to periostin inhibits ovarian tumor growth and metastasis" Mol Cancer Ther. Aug. 2011;10(8):1500-8. doi: 10.1158/1535-7163.MCT-11-0046. Epub Jun. 13, 2011. PMID: 21670235.
Field, S. et al., "Novel highly specific anti-periostin antibodies uncover the functional importance of the fascilin 1-1 domain and highlight preferential expression of periostin in aggressive breast cancer" (2016) Molecular Cancer Biology 138(8):1959-1970.
Kyutoku, M. et al., "Role of periostin in cancer progression and metastasis: inhibition of breast cancer progression and metastasis by anti-periostin antibody in a murine model" (2011) Int J Mol Med 28(2):181-6. doi: 10.3892/ijmm.2011.712.
Tai, I.T et al., "Periostin induction in tumor cell line explants and inhibition of in vitro cell growth by anti-periostin antibodies" (2005) Carcinogenesis 26(5):908-915, https://doi.org/10.1093/carcin/bgi034.
Orecchia, P. et al., "Identification of a novel cell binding site of periostin involved in tumour growth" (2011) Eur J Cancer 47(14):2221-9. doi: 10.1016/j.ejca.2011.04.026.
Extended European Search Report for European Patent Application No. 19772550.0 dated Jul. 6, 2022.
Sorensen, A. L. et al. Chemoenzymatically synthesized multimeric Tn/STn MUC1 glycopeptides elicit cancer-specific anti-MUC1 antibody responses and override tolerance. Glycobiology 16, 96-107, doi:10.1093/glycob/cwj044 (2006).
Staerz et al., "Hybrid antibodies can target sites for attack by T cells." Nature 314.6012 (1985): 628-631.
Steffensen, K.D., et al., Prevalence of epithelial ovarian cancer stem cells correlates with recurrence in early-stage ovarian cancer. J Oncol. 2011: p. 620523.
Swers, J.S., et al., Shuffled antibody libraries created by in vivo homologous recombination and yeast surface display. Nucleic Acids Res, 2004. 32(3): p. e36.
Tang, Y. et al. Periostin promotes migration and osteogenic differentiation of human periodontal ligament mesenchymal stem cells via the Jun amino-terminal kinases (JNK) pathway under inflammatory conditions. Cell proliferation, doi: 10.1111/cpr.12369 (2017).
Weaver-Feldhaus, J. M., et al. Directed evolution for the development of conformation-specific affinity reagents using yeast display. Protein engineering, design & selection : PEDS 18, 527-536, doi: 10.1093/protein/gzi060 (2005).
Yang, X., et al., Structures and biosynthesis of the N- and O-glycans of recombinant human oviduct-specific glycoprotein expressed in human embryonic kidney cells. Carbohydr Res, 2012. 358: p. 47-55.
Yun, H., et al. (1)H, (13)C, and (15)N resonance assignments of FAS1-IV domain of human periostin, a component of extracellular matrix proteins. Biomolecular NMR assignments 12, 95-98, doi: 10.1007/s12104-017-9786-z (2018).
Zhao, A., et al., Rapid isolation of high-affinity human antibodies against the tumor vascular marker Endosialin/TEM1, using a paired yeast-display/secretory scFv library platform. J Immunol Methods, 2011. 363(2): p. 221-32.

Shusta, E.V., et al., Directed evolution of a stable scaffold for T-cell receptor engineering. Nat Biotechnol, 2000. 18(7): p. 754-9.
Siegel, R.W., Antibody affinity optimization using yeast cell surface display. Methods Mol Biol, 2009. 504: p. 351-83.
Abbott, K. L. et al. Focused glycomic analysis of the N-linked glycan biosynthetic pathway in ovarian cancer. Proteomics 8, 3210-3220, doi:10.1002/pmic.200800157 (2008).
Abbott, K. L. et al. Identification of candidate biomarkers with cancer-specific glycosylation in the tissue and serum of endometrioid ovarian cancer patients by glycoproteomic analysis. Proteomics 10, 470-481, doi:10.1002/pmic.200900537 (2010).
Abbott, K. L. et al. Targeted glycoproteomic identification of biomarkers for human breast carcinoma. Journal of proteome research 7, 1470-1480, doi: 10.1021/pr700792g (2008).
Allam, H. et al. "Glycomic Analysis of Membrane Glycoproteins with Bisecting Glycosylation from Ovarian Cancer Tissues Reveals Novel Structures and Functions." Journal of Proteome Research 14.1 (2015): 434-446.
Allam, H. et al. The glycosyltransferase GnT-III activates Notch signaling and drives stem cell expansion to promote the growth and invasion of ovarian cancer. The Journal of biological chemistry, doi: 10.1074/jbc.M117.783936 (2017).
Alvero, A.B., et al., Molecular phenotyping of human ovarian cancer stem cells unravels the mechanisms for repair and chemoresistance. Cell Cycle, 2009. 8(1): p. 158-66.
Bapat, S.A., et al., Stem and progenitor-like cells contribute to the aggressive behavior of human epithelial ovarian cancer. Cancer Res, 2005. 65(8): p. 3025-9.
Bergan, L., et al. Development and in vitro validation of anti-mesothelin biobodies that prevent CA125/Mesothelin-dependent cell attachment. Cancer letters 255, 263-274, doi: 10.1016/j.canlet.2007.04.012 (2007).
Bhaumik, M., et al. Cloning and chromosomal mapping of the mouse Mgat3 gene encoding N-acetylglucosaminyltransferase III. Gene 164, 295-300 (1995).
Boder, E. T., et al. Directed evolution of antibody fragments with monovalent femtomolar antigen-binding affinity. Proceedings of the National Academy of Sciences of the United States of America 97, 10701-10705, doi:10.1073/pnas.170297297 (2000).
Boder, E. T., et al. Yeast surface display for screening combinatorial polypeptide libraries. Nat Biotechnol, 1997. 15(6): p. 553-7.
Bowley, D.R., et al., Antigen selection from an HIV-1 immune antibody library displayed on yeast yields many novel antibodies compared to selection from the same library displayed on phage. Protein Eng Des Sel, 2007. 20(2): p. 81-90.
Chandler, K. B., et al. Site-Specific N-Glycosylation of Endothelial Cell Receptor Tyrosine Kinase VEGFR-2. Journal of proteome research 16, 677-688, doi: 10.1021/acs.jproteome.6b00738 (2017).
Christiansen, M. N. et al. Cell surface protein glycosylation in cancer. Proteomics 14, 525-546, doi: 10.1002/pmic.201300387 (2014).
Colby, D. W. et al. Development of a human light chain variable domain (V(L)) intracellular antibody specific for the amino terminus of huntingtin via yeast surface display. Journal of molecular biology 342, 901-912, doi:10.1016/j.jmb.2004.07.054 (2004).
Colby, D. W. et al. Potent inhibition of huntingtin aggregation and cytotoxicity by a disulfide bond-free single-domain intracellular antibody. Proceedings of the National Academy of Sciences of the United States of America 101, 17616-17621, doi: 10.1073/pnas.0408134101 (2004).
Conway, S. J. et al. The role of periostin in tissue remodeling across health and disease. Cellular and molecular life sciences : CMLS 71, 1279-1288, doi: 10.1007/s00018-013-1494-y (2014).
Dangaj, D., et al. "Novel recombinant human b7-h4 antibodies overcome tumoral immune escape to potentiate T-cell antitumor responses." Cancer research 73.15 (2013): 4820-4829.
Dangaj, D., et al. Isolation and Validation of Anti-B7-H4 scFvs from an Ovarian Cancer scFv Yeast-Display Library. Methods in molecular biology 1319, 37-49, doi:10.1007/978-1-4939-2748-7_2 (2015).
Dangaj, D., et al. Mannose receptor (MR) engagement by mesothelin GPI anchor polarizes tumor-associated macrophages and is blocked by anti-MR human recombinant antibody. PLoS One, 2011. 6(12): p. e28386.

(56) References Cited

OTHER PUBLICATIONS

Doronina, S. O., et al. "Enhanced activity of monomethylauristatin F through monoclonal antibody delivery: effects of linker technology on efficacy and toxicity." Bioconjugate chemistry 17.1 (2006): 114-124.

Ghajar, C.M., et al., The perivascular niche regulates breast tumour dormancy. Nat Cell Biol, 2013. 15(7): p. 807-17.

Hakomori, S., et al. Isoantigenic expression of Forssman glycolipid in human gastric and colonic mucosa: its possible identity with "A-like antigen" in human cancer. Proceedings of the National Academy of Sciences of the United States of America 74, 3023-3027 (1977).

Hu, L., et al., Ovarian cancer stem-like side-population cells are tumourigenic and chemoresistant. Br J Cancer. 102(8); p. 1276-83. 2010.

International Searching Authority. International Search Report and Written Opinion for application PCT/US2019/023020. Mailed on Jun. 25, 2019.

Jia, L., et al., Proteomic analysis reflects different histologic subtypes of epithelial ovarian cancer. Med Hypotheses, 2012. 78(3): p. 407-9.

Kieke, M. C. et al. Selection of functional T cell receptor mutants from a yeast surface-display library. Proceedings of the National Academy of Sciences of the United States of America 96, 5651-5656 (1999).

Kohler, R. S. et al. Epigenetic activation of MGAT3 and corresponding bisecting GlcNAc shortens the survival of cancer patients. Oncotarget 7, 51674-51686, doi:10.18632/oncotarget. 10543 (2016).

Kubota, T., et al. Novel anti-Tn single-chain Fv-Fc fusion proteins derived from immunized phage library and antibody Fc domain. Anticancer research 30, 3397-3405 (2010).

Kurrey, N.K., et al., Snail and slug mediate radioresistance and chemoresistance by antagonizing p53-mediated apoptosis and acquiring a stem-like phenotype in ovarian cancer cells. Stem Cells, 2009. 27(9): p. 2059-68.

Kusumbe, A.P., et al., CD133-expressing stem cells associated with ovarian metastases establish an endothelial hierarchy and contribute to tumor vasculature. Stem Cells, 2009. 27(3): p. 498-508.

Lakshminarayanan, V. et al. Immune recognition of tumor-associated mucin MUC1 is achieved by a fully synthetic aberrantly glycosylated MUC1 tripartite vaccine. Proceedings of the National Academy of Sciences of the United States of America 109, 261-266, doi:10.1073/pnas.1115166109 (2012).

Lee, K. J. et al. Phage-display selection of a human single-chain fv antibody highly specific for melanoma and breast cancer cells using a chemoenzymatically synthesized G(M3)-carbohydrate antigen. Journal of the American Chemical Society 124, 12439-12446 (2002).

Li, W. et al. Periostin: its role in asthma and its potential as a diagnostic or therapeutic target. Respiratory research 16, 57, doi: 10.1186/s12931-015-0218-2 (2015).

Li, Y., et al., Validation of glypican-3-specific scFv isolated from paired display/secretory yeast display library. BMC Biotechnol, 2012. 12: p. 23.

Liu, J. et al. Structural characterizations of human periostin dimerization and cysteinylation. FEBS letters 592, 1789-1803, doi:10.1002/1873-3468.13091 (2018).

Lu, Z., et al. "Generation of a fully human scFv that binds tumor-specific glycoforms." Scientific reports 9.1 (2019): 1-11.

Mao, S. et al. Phage display library selection of high-affinity human single-chain antibodies to tumor-associated carbohydrate antigens sialyl Lewisx and Lewisx. Proceedings of the National Academy of Sciences of the United States of America 96, 6953-6958 (1999).

Milstein, et al. "Hybrid hybridomas and their use in immunohistochemistry." Nature 305.5934 (1983): 537-540.

Nitta et al. "Preliminary trial of specific targeting therapy against malignant glioma." The Lancet 335.8686 (1990): 368-371.

North, S.J., et al., Glycomics profiling of Chinese hamster ovary cell glycosylation mutants reveals N-glycans of a novel size and complexity. J Biol Chem, 2010. 285(8): p. 5759-75.

Posey Jr, A. D., et al. "Engineered Car T cells targeting the cancer-associated Tn-glycoform of the membrane mucin MUC1 control adenocarcinoma." Immunity 44.6 (2016): 1444-1454.

Prantner, A. M. et al. Molecular Imaging of Mesothelin-Expressing Ovarian Cancer with a Human and Mouse Cross-Reactive Nanobody. Molecular pharmaceutics 15, 1403-1411, doi: 10.1021/acs.molpharmaceut.7b00789 (2018).

Ragupathi, G. Carbohydrate antigens as targets for active specific immunotherapy. Cancer immunology, immunotherapy : CII 43, 152-157 (1996).

Rosenberg SA et al. "Adoptive cell transfer: a clinical path to effective cancer immunotherapy." Nature Reviews Cancer 8.4 (2008): 299-308.

Scholler, N., et al., Bead-based ELISA for validation of ovarian cancer early detection markers. Clin Cancer Res, 2006. 12(7 Pt 1): p. 2117-24.

Scholler, N., et al., Method for generation of in vivo biotinylated recombinant antibodies by yeast mating. J Immunol Methods, 2006. 317(1-2): p. 132-43.

Scholler, N., Selection of antibody fragments by yeast display. Methods Mol Biol, 2012. 907: p. 259-80.

Siegel RW. et al., High efficiency recovery and epitope-specific sorting of an scFv yeast display library, J Immunol Methods, 2004, vol. 286, pp. 141-153.

Almagro et al., Humanization of antibodies, Frontiers in Bioscience, 2008, vol. 13, pp. 1619-1633.

* cited by examiner

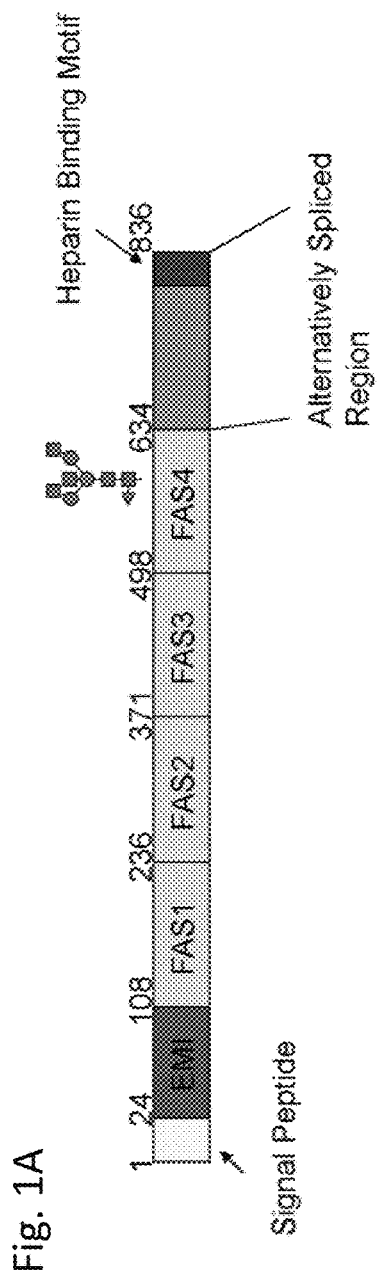
Fig. 1A
Fig. 1B
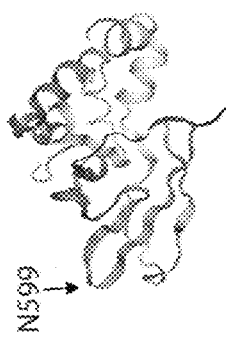
Fig. 1C
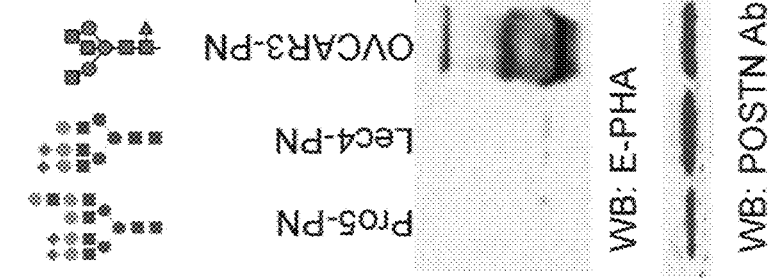

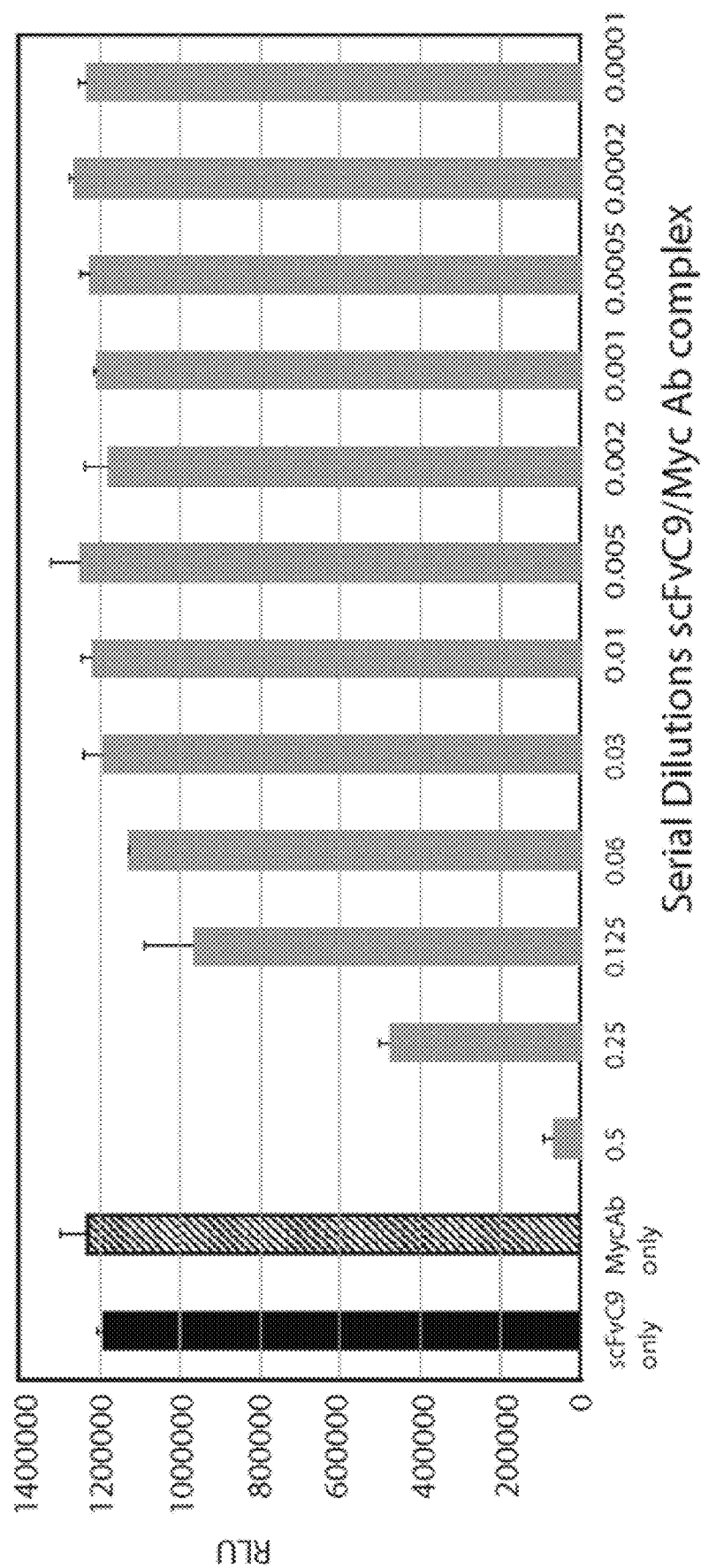

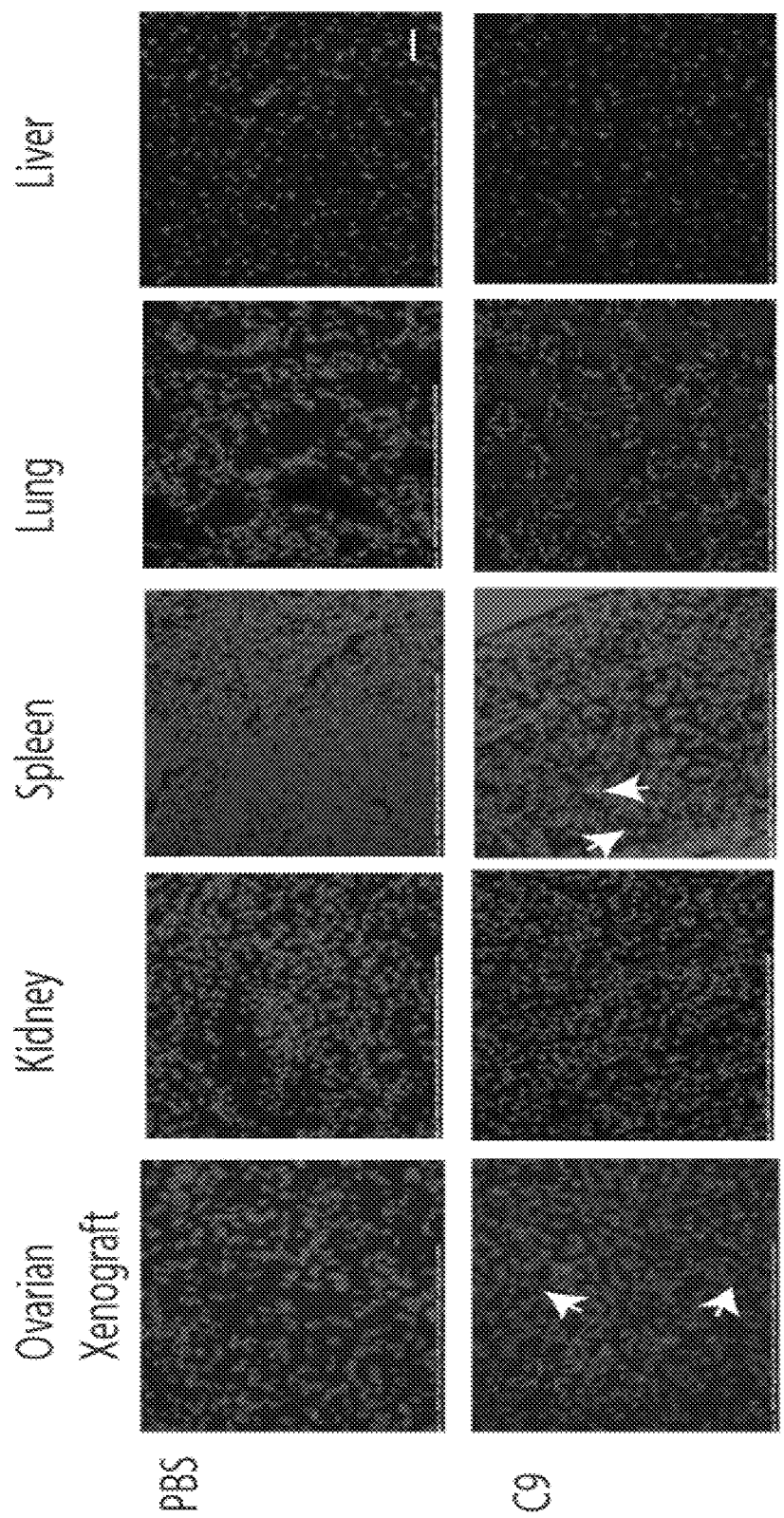

Fig. 7B
Mg beads only
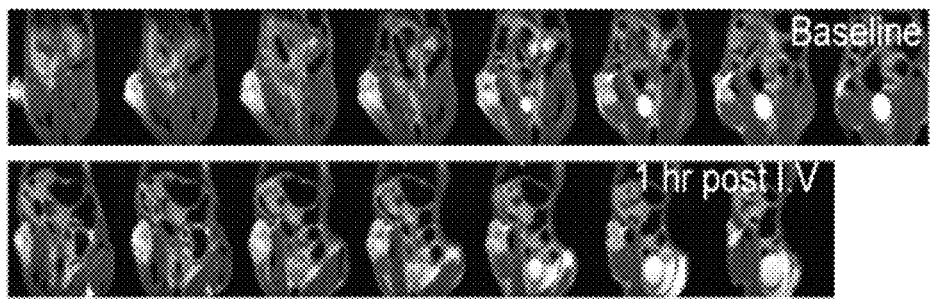
C9 + Mg Beads
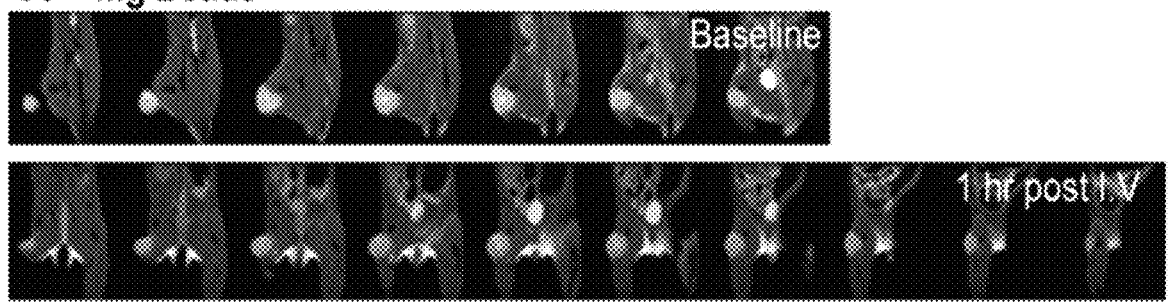
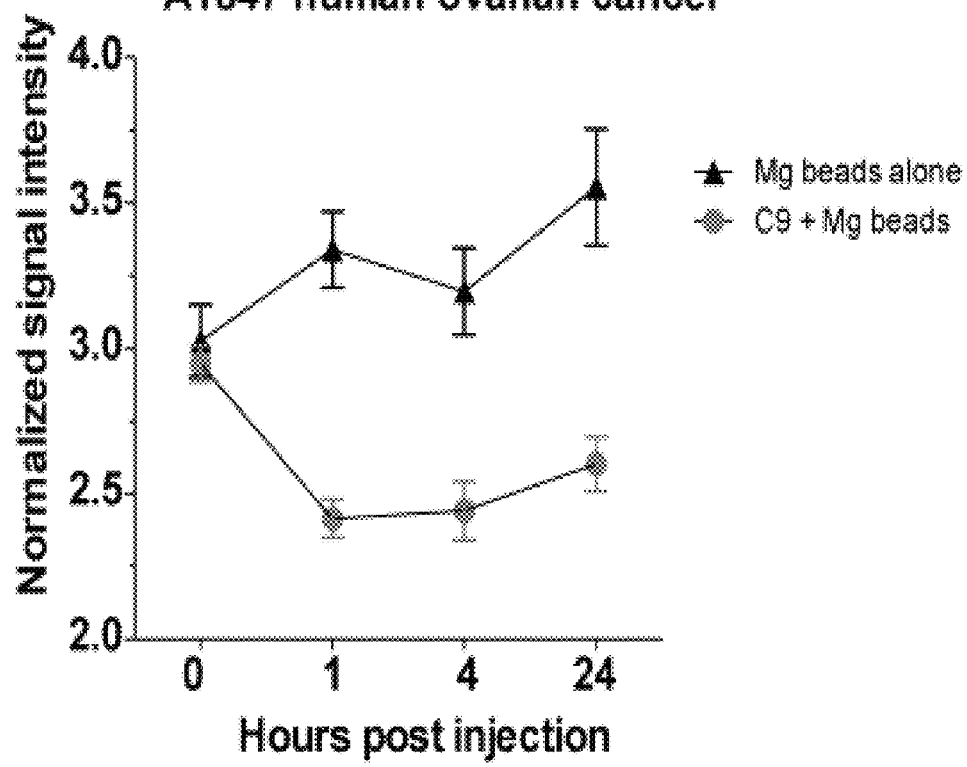

3 scab on the abdomen

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: Synthetic: CDR H1 Protein Sequence of C9

<400> SEQUENCE: 1

Gly Phe Ile Phe Asp Asp Tyr Ala Met His
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic: CDR H2 Protein Sequence of C9

<400> SEQUENCE: 2

Asn Ser Gly His Ile Asp Tyr Ala Asp Ser Val Glu Gly Arg Phe Thr
```

<210> SEQ ID NO 3
<211> LENGTH: 12
<212> TYPE: PRT
<213> ORGANISM: Artificial Sequence
<220> FEATURE:
<223> OTHER INFORMATION: Synthetic: CDR H3 Protein Sequence of C9

<400> SEQUENCE: 3

Val Ser Tyr Leu Ser Thr Ala Ser Ser Leu Asp Tyr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic: CDR L3 Protein Sequence of C9

<400> SEQUENCE: 4

Gln Arg Tyr Asn Arg Ala Pro Tyr Thr
1               5

<210> SEQ ID NO 5
<211> LENGTH: 137
<212> TYPE: PRT
<213> ORGANISM: Artificial Sequence
<220> FEATURE:
<223> OTHER INFORMATION: Synthetic: Heavy Chain Variable Region Protein
      Sequence of C9

<400> SEQUENCE: 5

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Phe Glu Gly Ser Glu Gln Lys
    130                 135

<210> SEQ ID NO 6
<211> LENGTH: 48
<212> TYPE: PRT
<213> ORGANISM: Artificial Sequence
<220> FEATURE:
<223> OTHER INFORMATION: Synthetic: Light Chain Variable Region Protein
      Sequence of C9

<400> SEQUENCE: 6

Gly Ser Asp Phe Thr Leu Thr Ile Ser Ser Leu Gln Pro Glu Asp Val
1               5                   10                  15

Ala Thr Tyr Tyr Cys Gln Arg Tyr Asn Arg Ala Pro Tyr Thr Phe Gly
            20                  25                  30

Gln Gly Thr Lys Val Glu Ile Lys Arg Thr Val Ala Ala Pro Ser Val
        35                  40                  45

<210> SEQ ID NO 7
<211> LENGTH: 225
<212> TYPE: PRT
<213> ORGANISM: Artificial Sequence
<220> FEATURE:
<223> OTHER INFORMATION: Synthetic: Protein Sequence of C9 scFv

<400> SEQUENCE: 7

Leu Gly Gly Gly Gly Ser Gly Gly Gly Ser Gly Ser Asp Phe Thr
1               5                   10                  15

Leu Thr Ile Ser Ser Leu Gln Pro Glu Asp Val Ala Thr Tyr Tyr Cys
            20                  25                  30

Gln Arg Tyr Asn Arg Ala Pro Tyr Thr Phe Gly Gln Gly Thr Lys Val
        35                  40                  45

Glu Ile Lys Arg Thr Val Ala Ala Pro Ser Val Gly Gly Ser Ser Arg
    50                  55                  60

Ser Ser Ser Gly Gly Gly Ser Gly Gly Gly Gly Gln Val Gln
65                  70                  75                  80

Leu Val Gln Ser Gly Gly Leu Val Gln Pro Gly Arg Ser Leu Arg
                85                  90                  95

Leu Ser Cys Ala Ala Ser Gly Phe Ile Phe Asp Asp Tyr Ala Met His
            100                 105                 110

Trp Val Arg Gln Ala Pro Gly Lys Gly Leu Glu Trp Val Ser Ala Ile
        115                 120                 125

Thr Trp Asn Ser Gly His Ile Asp Tyr Ala Asp Ser Val Glu Gly Arg
    130                 135                 140

Phe Thr Ile Ser Arg Asp Asn Ala Lys Asn Ser Leu Tyr Leu Gln Met
145                 150                 155                 160

Asn Ser Leu Arg Ala Glu Asp Thr Ala Val Tyr Tyr Cys Ala Lys Val
                165                 170                 175

Ser Tyr Leu Ser Thr Ala Ser Ser Leu Asp Tyr Trp Gly Gln Gly Thr
            180                 185                 190

Leu Val Thr Val Ser Ser Ala Ser Thr Lys Gly Pro Ser Val Phe Phe
        195                 200                 205

Glu Gly Ser Glu Gln Lys Gly Lys Pro Ile Pro Asn Pro Leu Leu Gly
    210                 215                 220

Leu
225

<210> SEQ ID NO 8
<211> LENGTH: 675
<212> TYPE: DNA
<213> ORGANISM: Artificial Sequence
<220> FEATURE:
<223> OTHER INFORMATION: Synthetic: DNA Sequence of C9 scFv

<400> SEQUENCE: 8
ctgggtggtg gaggttctgg tggtggtgga tctgggtcag atttcactct caccatcagc        60
agcctacagc ctgaagatgt tgcaacttat tactgtcaaa ggtataaccg tgcaccgtat       120
acttttggcc aggggaccaa ggtggaaatc aaacgaactg tggctgcacc atctgtcggc       180
ggatcctcta ggtcaagttc cagcggcggc ggtggcagcg gaggcggcgg tcaggtgcag       240

-continued

```
ctggtgcagt ctgggggagg cttggtacag cccggcaggt ccctgagact ctcctgtgcg    300
gcctctggat tcatctttga tgattatgcc atgcactggg tccggcaagc tccagggaag    360
ggcctggaat gggtctcagc tatcacttgg aatagtggtc acatagacta tgcggactct    420
gtggagggcc gattcaccat ctccagagac aacgccaaga actccctgta tctgcaaatg    480
aacagtctga gagctgagga tacggccgta tattattgtg cgaaagtctc gtaccttagc    540
accgcgtcct cccttgacta ttggggccaa ggtaccctgg tcaccgtctc gagtgcctcc    600
accaagggcc catcggtctt cttcgaggga tccgaacaaa agggtaagcc tatccctaac    660
cctctcctcg gtctc                                                      675
```

<210> SEQ ID NO 9
<211> LENGTH: 836
<212> TYPE: PRT
<213> ORGANISM: Homo sapiens
<220> FEATURE:
<221> NAME/KEY: misc_feature
<223> OTHER INFORMATION: Human Periostin Protein Sequence including 21
      amino acid N-terminal signal peptide

<400> SEQUENCE: 9

```
Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270
```

```
Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
    290                 295                 300

Ile Leu Asn Thr Leu Gln Cys Ser Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
                355                 360                 365

Ser Ala Lys Gln Val Ile Glu Leu Ala Gly Lys Gln Gln Thr Thr Phe
        370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685
```

-continued

```
Leu Gln Pro Ile Ile Lys Thr Glu Gly Pro Thr Leu Thr Lys Val Lys
    690             695             700
Ile Glu Gly Glu Pro Glu Phe Arg Leu Ile Lys Glu Gly Glu Thr Ile
705             710             715                 720
Thr Glu Val Ile His Gly Glu Pro Ile Ile Lys Lys Tyr Thr Lys Ile
            725             730             735
Ile Asp Gly Val Pro Val Glu Ile Thr Glu Lys Glu Thr Arg Glu Glu
            740             745             750
Arg Ile Ile Thr Gly Pro Glu Ile Lys Tyr Thr Arg Ile Ser Thr Gly
        755             760             765
Gly Gly Glu Thr Glu Glu Thr Leu Lys Lys Leu Leu Gln Glu Glu Val
    770             775             780
Thr Lys Val Thr Lys Phe Ile Glu Gly Gly Asp Gly His Leu Phe Glu
785             790             795             800
Asp Glu Glu Ile Lys Arg Leu Leu Gln Gly Asp Thr Pro Val Arg Lys
            805             810             815
Leu Gln Ala Asn Lys Lys Val Gln Gly Ser Arg Arg Arg Leu Arg Glu
            820             825             830
Gly Arg Ser Gln
        835
```

PERIOSTIN ANTIBODIES AND METHODS OF USING THE SAME

CROSS REFERENCE TO RELATED APPLICATIONS

This application is a national stage filing under 35 U.S.C. 371 of International Application No. PCT/US2019/023020, filed Mar. 19, 2019, which claims priority to U.S. Provisional Patent Application No. 62/644,681, filed Mar. 19, 2018 and U.S. Provisional Application No. 62/727,915, filed Sep. 6, 2018, all of which are incorporated herein by reference in their entireties.

STATEMENT REGARDING FEDERALLY SPONSORED RESEARCH

This invention was made with United States government support awarded by the United States National Institute of Health ("NIH") grant number UO1CA168870-01. The United States has certain rights in this invention.

SEQUENCE LISTING

A Sequence Listing accompanies this application. The sequences are listed by SEQ ID NO: in the specification and the corresponding sequences are found in the Sequence Listing filed herewith which is incorporated herein by reference. This application is being filed electronically and includes an electronically submitted Sequence Listing in .txt format. The .txt file contains a sequence listing entitled "2019-03-19_169852-00002_Sequence_Listing.txt" created on Mar. 19, 2019 and is 13300 bytes in size. The Sequence Listing contained in this .txt file is part of the specification and is hereby incorporated by reference herein in its entirety.

INTRODUCTION

Antibody-based therapy and diagnosis of cancer has become an important strategy for treating and diagnosing cancer patients. Cell surface antigens that are selectively expressed by cancer cells as compared to normal cells provide an attractive means of developing targeted cancer therapies and diagnostic tools. A key challenge in the field, however, has been to identify antigens that may be used to selectively target cancer cells. Peptide antigens are commonly used to develop cancer cell-specific antibodies although the applicability of such antigens may be limited in certain contexts, for example, when the expression of the peptide antigen is similar in normal and cancer cells.

Cancer-specific glycosylation changes in proteins are another attractive group of antigens that may be able to distinguish cancer cells from normal cells and may be useful in the development of both diagnostic and therapeutic applications. Few antibodies, however, have been developed that specifically target the carbohydrate moieties that are selectively expressed on cancer cells. Thus, there remains a need in the art for new antibodies that specifically target glycosylation differences between cancer cells and normal cells.

SUMMARY

In one aspect of the present invention, antigen-binding reagents are provided. The antigen-binding reagents may specifically bind to a human Periostin glycoprotein, preferably, a glycan epitope of the human Periostin glycoprotein. In some embodiments, the antigen-binding reagent may include the following complementarity-determining regions (CDRs): CDR H1, GFIFDDYAMH (SEQ ID NO: 1), CDR H2, NSGHIDYADSVEGRFT (SEQ ID NO: 2), CDR H3, VSYLSTASSLDY (SEQ ID NO: 3), CDR L3, QRYN-RAPYT (SEQ ID NO: 4) or a heavy chain variable region comprising SEQ ID NO: 5 and a light chain variable region comprising SEQ ID NO: 6.

In another aspect, antigen-binding conjugates are provided. The antigen-binding conjugates may include any one of the antigen-binding reagents described herein linked to an agent.

In a further aspect, cells are provided. The cells may include any of the antigen-binding reagents or any of the antigen-binding conjugates described herein.

In another aspect, pharmaceutical compositions are provided. The pharmaceutical compositions may include any of the antigen-binding reagents, any of the antigen-binding conjugates, or any of the cells disclosed herein and a pharmaceutical carrier, excipient, or diluent.

In another aspect, the present invention relates to methods for imaging cancer cells in a subject. The methods may include administering in an effective amount any of the antigen-binding reagents, any of the antigen-binding conjugates, or any of the pharmaceutical compositions described herein to the subject, and generating an image of at least a portion of the subject using an imaging modality. Preferably in these method embodiments, the imaging of cells bound to the antigen-binding reagent, antigen-binding conjugate, or pharmaceutical composition is indicative of the cells being cancer cells.

In a further aspect, the present invention relates to methods of detecting cancer cells in a subject sample. The methods may include obtaining a sample from the subject, contacting the sample with any of the antigen-binding reagents or any of the antigen-binding conjugates disclosed herein, and detecting binding of the antigen-binding reagent or antigen-binding conjugate to cells in the sample. Suitably, binding of the antigen-binding reagent or the antigen-binding conjugate to the cells is indicative of the cells being cancer cells.

In a still further aspect, the present invention relates to methods of treating cancer cells in a subject. The methods may include administering to the subject an effective amount any of the antigen-binding reagents, any of the antigen-binding conjugates, any of the cells, or any of the pharmaceutical compositions disclosed herein to treat the cancer in the subject.

BRIEF DESCRIPTION OF DRAWINGS

FIG. 1A-1C shows the Periostin domain structure and location of complex N-linked glycosylation. FIG. 1A shows the Domain map of the human periostin protein with the glycosylation site in the last FAS1 domain marked. FIG. 1B shows the NMR structure (PDB 5WT7) of the FAS4 domain showing the unstructured loop where asparagine 599 is located[35]. Crystal structure (PDB 5YJG) of the FAS1-FAS4 domains for human periostin with the N599 solvent exposed[34]. FIG. 1C is a Western blot analysis of periostin protein purified from culture supernatant on anti-Flag resin. The top cropped image is detected using the lectin E-PHA (Vector Labs) and the bottom cropped image is the detection of the same blot with periostin antibody (Santa Cruz Biotechnologies). Examples of previously detected glycan structures for each cell line are shown above each lane[3,39].

FIG. 4A-FIG. 4E shows the specificity, cellular localization and antibody-dependent cytotoxicity for scFvC9 biobody. FIG. 4A shows Flow cytometry analysis of OVCAR3-PN Control ShRNA and OVCAR3-PN GnT-III ShRNA cells stained with scFvC9 biobody premixed with streptavidin APC (labeled with 1) or streptavidin APC only (labeled with 2). FIG. 4B shows representative images of scFvC9 biobody binding and internalization into OVCA26 cells, bar 10 μm. FIG. 4C shows functional analysis of cell cytotoxicity using a cell titer glow luminescence viability assay. ScFvC9 biobody was premixed with anti-myc mAb and serial dilutions were added to cell for 48 hr at 37° C. The results shown are representative of 3 independent experiments. FIG. 4D and FIG. 4E shows scFvC9 cell binding and specificity in human glioblastoma cells. FIG. 4D shows Crispr/Cas9 KO of the Mgat3 gene in single cell isolated LN18 clone known as C2 is confirmed by the absence of E-PHA binding indicating a loss of bisecting N-glycan. The non-targeted single cell isolated clone known as control A1 has Mgat3 expression confirmed by the binding of E-PHA lectin, bar 20 μm. FIG. 4E shows the scFv C9 biobody binds to LN18 Control A1 clone and has no binding to the LN18 Crispr/Cas9 Mgat3 KO clone C2.

FIG. 6 shows the detection of scFvC9 biobody in tumors and tissues at the 24 hr time point. Immune compromised female NSG mice with subcutaneous A1847 xenograft tumors were injected with scFvC9 biobody IV 24 hr before necropsy and tissue collection. Sections were stained with Streptavidin Qdot (1:50 in 1×PBS) prior to counterstain with DAPI. White arrows mark regions of interest discussed in the text, Bar 100 μm.

FIG. 7A and FIG. 7B shows the MR studies with scFvC9 biobody. FIG. 7A shows the phantom tubes layered with cells only, anti-flag magnetic bead only, or cells with scFvC9 biobody and anti-flag magnetic beads were MR imaged. Representative image shown and results in graph to the right represent mean decreased signal intensity from 3 independent experiments, ±SEM P<0.0001. FIG. 7B shows Immune compromised NSG female mice with A1847 subcutaneous tumor were injected with scFvC9 coupled 1:2 with magnetic avidin beads. Representative 1 hour images are shown and cumulative normalized (SI tumor/SI muscle for given ROI) signal intensity for each time point are graphed to the right.

DETAILED DESCRIPTION

Figure 2:
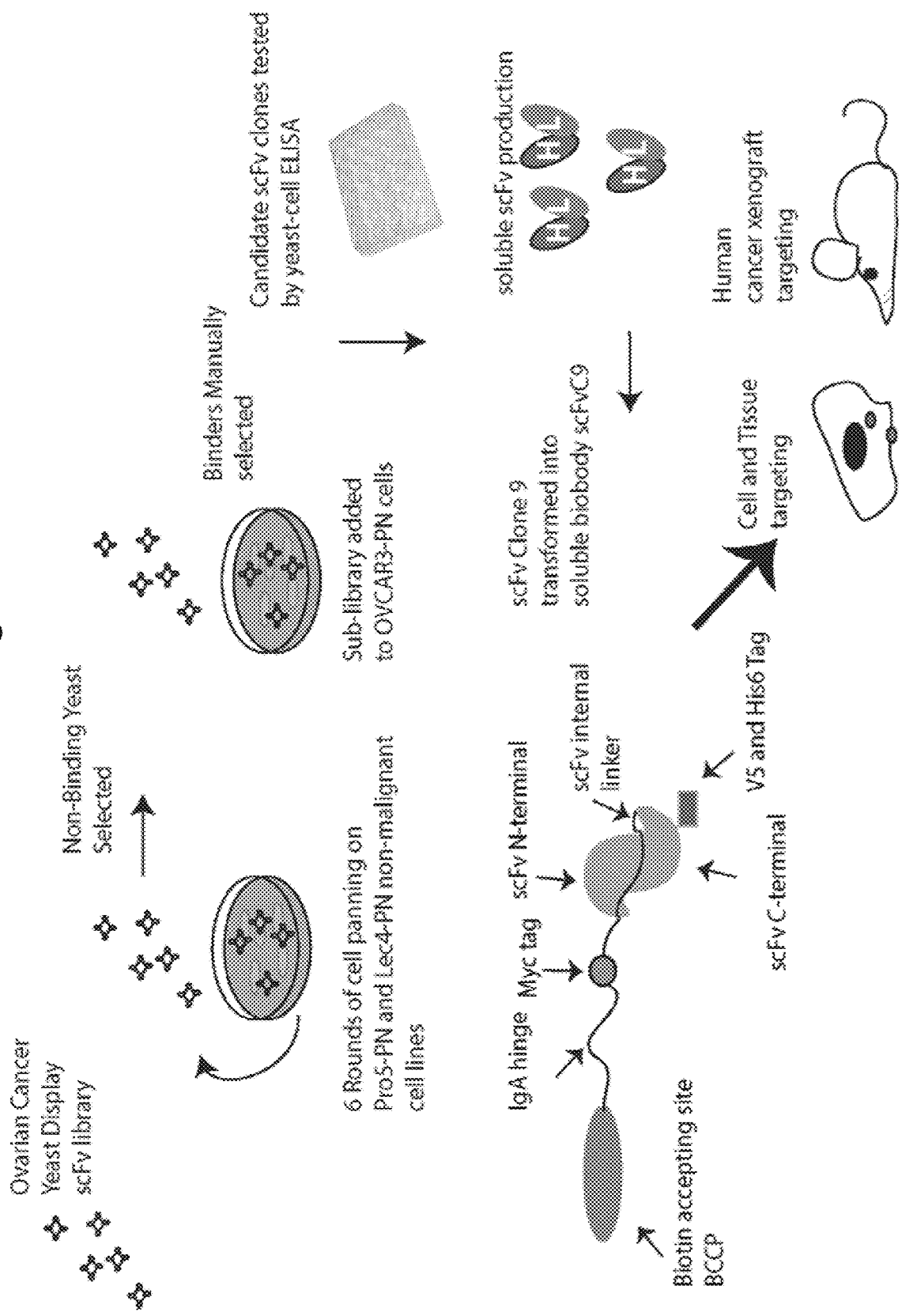
FIG. 2 shows a schematic flow of the selection, purification, and validation approach. The ovarian cancer yeast-display scFv library was first subtracted using 6 rounds each on the non-malignant Pro5-PN and Lec4-PN cells. Non-binders were grown and added to OVCAR3-PN cells for multiple rounds of selection. Clonal populations of binders were evaluated using yeast-cell ELISA and yeast that had binding specificity for bisecting glycans were made into secreted scFv. Clone 9 was converted to a biotin labeled antibody known as a biobody with the indicated tags and evaluated using cell lines and xenograft tumor models.

Here, the present inventors have developed antigen-binding reagents that recognize a cancer-specific glycan (carbohydrate) modification on the human Periostin protein. In a previous study, the present inventors discovered an unusual bisecting N-linked glycan structure on the human Periostin protein that is specifically expressed in cancer cells such as ovarian cancer cells. See Abbott et al., *Proteomics* 10(3): 470-481 (2010). The N-linked glycan structure is unusual due to the lack of galactose capping and sialic acid extensions and has been described, for example, in Allam, Heba et al. "Glycomic Analysis of Membrane Glycoproteins with Bisecting Glycosylation from Ovarian Cancer Tissues Reveals Novel Structures and Functions." *Journal of Proteome Research* 14.1 (2015): 434-446. PMC.

Tumor cells typically display tumor-specific changes in glycosylation on surface glycoproteins and glycolipids that can serve as biomarkers for diagnosis as well as candidates for immunotherapy[1-4]. Such changes in glycosylation are due to altered expression levels of unique glycosyltransferases and glycoproteins that lead to their surface expression and potential secretion from tumor cells. However, this area of research has been hampered by having only a few specific anti-carbohydrate antibodies useful for targeting tumor cell-specific changes in glycosylation.

One approach to develop such specific anti-carbohydrate antibodies is yeast display. These technologies can improve the affinity and specificity of recognition reagents[5-7]. In this method, recombinant antibodies are displayed on the yeast surface as a fusion protein to a cell wall component (Aga-2) and library generation is facilitated by the homologous recombination system inherent in yeast[8,9]. Coupling flow cytometry with cell surface display of recombinant antibodies expressed as single chain Fragment variables (scFv) permits the monitoring of both scFv expression at the yeast surface and scFv binding to the antigen[10]. Yeast display has also proven to be highly effective for various directed evolution applications[11-15]. These methods translate into time- and cost-efficient production and screening of scFvs that have enabled the identification of many functional scFvs directed toward numerous medically relevant proteins, including scFv directed against mesothelin[16], TEM1[17], mannose receptor[18], glypican[19], and B7-H4[20].

We have utilized the powerful advantages of the yeast display method to isolate scFv that recognize the tumor-specific bisecting glycan structures discovered in ovarian cancer[3]. These glycans are generated in part by a unique glycosyltransferase GnT-III, encoded by the Mgat3 gene, which creates bisecting complex-type N-glycans by addition of a β1-4-linked GlcNAc to the core β-mannose of N-glycans[21]. We previously discovered that the Mgat3 gene was highly amplified in ovarian cancer[22]. The Mgat3 gene is amplified in several human cancers due to hypomethylation changes in the promoter near the transcription start site[23]. The structures of bisecting N-glycans in ovarian cancer are different than those bisecting N-glycans found in non-malignant cells. Unexpectedly, the bisecting N-glycans from ovarian cancers show reduced branching, lack of galactose and sialic acid, with or without core fucose making this glycan structure a biomarker for ovarian cancer and possibly several other human cancers[3].

Our laboratory has used a targeted glycoproteomic approach to identify glycoproteins that carry tumor-associated bisecting glycan structures in ovarian cancer. Our analysis of secreted and membrane proteins from primary ovarian cancer tissues led to the discovery of periostin, also known as osteoblast-specific factor 2 (OSF-2) as a potential biomarker[3,24]. Periostin is a secreted glycoprotein that is present in circulation and also associates with the cell membranes evidenced by the presence of periostin in membrane fractions by proteomic analysis[3]. The likely mechanism of cell surface binding is due to presence of FAS1 domains that have been demonstrated to interact with the membrane in the protein fasciclin[25]. Despite the elevated levels of periostin in human cancers, this glycoprotein has not been utilized as a biomarker due to variable expression in inflammatory conditions[26-28]. This complicates the use of the protein itself as a biomarker for cancer because detection of the periostin protein levels may not correlate with the disease burden. The ability to detect the cancer-specific bisecting glycoform on periostin would be a superior biomarker for diagnostic applications and may lead to the development of new therapeutic approaches. Here, we describe our subtraction/selection process to identify a yeast-displayed scFv (scFvC9) and characterization of its specificity for tumor-specific bisecting glycan structures. We further validate the use of scFvC9 to target ovarian cancer xenograft tumors in vivo. Together these finding suggest the potential use for this antibody in diagnostic and therapeutic applications for cancers that have amplification of the Mgat3 gene.

Briefly, the present inventors produced cell lines that eliminate the enzyme that adds the bisecting glycan as well as control cell lines that produce this enzyme. They also produced a mutant version of the human periostin protein that is missing the N-linked glycosylation site. Using these cell lines, they developed a selective panning strategy for use with a scFv yeast display library derived from B cells of ovarian cancer patients. To subtract scFvs that interact with the peptide portion of the human periostin protein or interact with other glycan structures, they first panned with the cell lines that do not express the bisecting glycans yet express the periostin protein. Next, they panned with cell lines that express bisecting glycans and express the periostin protein to select scFvs that bind to the N-linked glycosylation moiety. These binders were then further screened to select clones that specifically bind to the glycan. One of the positive clones, known as C9, was further characterized and shown to specifically target the cancer-specific N-linked glycan structure on the human periostin protein and to specifically target human xenograft ovarian and lung tumors growing in several mouse cancer models. Based on this data, it becomes readily apparent that the C9 scFv may serve as the basis for the antigen-binding reagents disclosed herein, which may further be used in a variety of compositions and methods.

Antigen-Binding Reagents

In one aspect of the present invention, antigen-binding reagents are provided. As used herein, the term "antigen-binding reagent(s)" is used in the broadest sense to refer to polypeptide affinity agents based on antibodies. For example, the antigen-binding reagent may include, without limitation, a single chain antibody (e.g., single-chain Fvs (scFvs), biobodies, disulfide-linked Fvs (sdFvs), etc.) monoclonal antibody, or antibody fragments such as Fab, Fab', F(ab')$_2$, Fv fragments, diabodies, linear antibodies, or multispecific antibodies (e.g., bispecific antibodies) formed from antibody fragments. The antigen-binding reagent may be a chimeric, a humanized, or a fully human polypeptide sequence. The antigen-binding reagent may be any one of the known major classes of immunoglobulins including IgA, IgD, IgE, IgG, IgY, and IgM, any class (e.g., IgG1, IgG2, IgG3, IgG4, IgA1 and IgA2), or any subclass (e.g., IgG2a and IgG2b) of immunoglobulin molecules. In some embodiments, the antigen-binding reagent may be a scFv, a Fab, or an IgG monoclonal antibody.

The antigen-binding reagents include amino acid residues that interact with an "antigen" such as the human Periostin protein and confer on the antigen-binding reagent the capability of specifically binding to the antigen. An "antigen" is a molecule or a portion of a molecule capable of being bound by an antibody. An antigen may have one or more than one epitope. An "epitope" refers to that portion of any molecule capable of being recognized by, and bound by, an antigen-binding reagent. Generally, epitopes include a surface grouping of molecules, for example, amino acids or carbohydrate moeities that form a specific three-dimensional structure recognized by the antigen-binding reagent.

The antigen-binding reagents further may include the "framework" amino acid residues necessary to maintain the proper conformation of the antigen-binding amino acid residues and/or amino acid residues commonly found in some types of antibodies that modulate the immune system (e.g., Fc effector functions such as complement-dependent cytotoxicity (CDC), antibody-dependent cellular cytotoxicity (ADCC), and/or antibody-dependent cell phagocytosis (ADCP)).

The antigen-binding amino acid residues of the antigen-binding reagents are commonly known as the "complementarity determining regions" or "CDR" regions. These CDR regions account for the basic specificity of the antigen-binding reagent for a particular antigenic determinant structure. The CDRs are non-contiguous stretches of amino acids within the variable regions of antibodies. The variable heavy and light chains of some antibodies each have three CDR regions, each non-contiguous with the others (termed L1, L2, L3, H1, H2, H3) for the respective light (L) and heavy (H) chains. Surprisingly, the present inventors have found that the C9 biobody disclosed in the Examples contains three heavy chain CDR regions (H1, H2, H3) and only a single light chain CDR region (L3).

The antigen-binding reagent may be capable of specifically binding to a human Periostin glycoprotein. Periostin (also known as POSTN, PN, or osteoblast-specific factor OSF-2) is a human glycoprotein that functions as a ligand for alpha-V/beta-3 and alpha-V/beta-5 integrins to control cell motility. Periostin is also known to be glycosylated and, in a previous study, the present inventors discovered an unusual bisecting N-linked glycan structure on the human Periostin protein that is specifically expressed in cancer cells such as ovarian cancer cells. See Abbott et al., *Proteomics* 10(3): 470-481 (2010). An exemplary protein sequence of human Periostin including an N-terminal sequence peptide is provided as SEQ ID NO: 9.

Optionally, the antigen-binding reagent may specifically bind to a human Periostin glycoprotein with an affinity of at least $10^{-6}$ M, $10^{-7}$ M, $10^{-8}$ M, $10^{-9}$ M, $10^{-10}$ M, or $10^{-11}$ M. Methods for determining the affinity of an antigen-binding reagent are known by those of ordinary skill in the art. See, e.g., Antibodies: A Lab. Manual (Harlow et al., eds., Cold Spring Harbor Lab. Press, Cold Spring Harbor, N.Y., 1988).

The antigen-binding reagent may specifically bind to a glycan epitope of the human Periostin glycoprotein. The glycan epitope may be specifically present on Periostin glycoproteins present on cancer cells. In some embodiments, the glycan epitope includes an N-linked glycan structure.

In accordance with the present invention, cancer cells may include, without limitation, epithelial cancer cells, ovarian cancer cells, lung cancer cells, breast cancer cells, pancreatic cancer cells, prostate cancer cells, bladder cancer cells, gastric cancer cells, esophageal cancer cells, colon cancer cells, skin cancer cells, testicular cancer cells, colorectal cancer cells, urothelial cancer cells, renal cancer cells, hepatocellular cancer cells, leukemia cancer cells, lymphoma cancer cells, multiple myeloma cancer cells, and central nervous system cancer cells.

The antigen-binding reagent may include the following complementarity-determining regions (CDRs): CDR H1, GFIFDDYAMH (SEQ ID NO: 1), CDR H2, NSGHIDY-ADSVEGRFT (SEQ ID NO: 2), CDR H3, VSYL-STASSLDY (SEQ ID NO: 3), CDR L3, QRYNRAPYT (SEQ ID NO: 4). In some embodiments, the antigen-binding reagent may include a heavy chain variable region including SEQ ID NO: 5 and a light chain variable region including SEQ ID NO: 6. In some embodiments, the antigen-binding reagent may include SEQ ID NO: 7 (C9 scFv protein sequence).

Antigen-Binding Conjugates

In another aspect of the present invention, antigen-binding conjugates are provided. The antigen-binding conjugates may include any one of the antigen-binding reagents described herein linked to an agent. An "agent" may be any substance that provides additional functionality to the antigen-binding reagents. Suitable agents include, without limitation, detectable imaging agents, therapeutic agents, immunoprotein domains, or combinations thereof.

A "detectable imaging agent" may be any suitable chemical or substance that may be detected as a signal or contrast using imaging techniques. Suitable detectable imaging agents may be, without limitation, a fluorophore moiety, an enzyme moiety, an optical moiety, a magnetic moiety, a radiolabel moiety, an X-ray moiety, an ultrasound imaging moiety, a nanoparticle-based moiety, or a combination of two or more of the listed moieties.

A "fluorophore moeity" may include any molecule capable of generating a fluorescent signal. Various fluorophore moieties are well-known in the art and/or commercially available. Exemplary fluorophore moeities include, without limitation, fluorescein, FITC, Alexa Fluor 488, Alexa Fluor 660, Alexa Fluor 680, Alexa Fluor 750, and Alexa Fluor 790 (Life Technologies); Cy2, Cy3, Cy3.5, Cy5, Cy5.5 and Cy7 (GE Healthcare); DyLight 350, DyLight 488, DyLight 594, DyLight 650, DyLight 680, DyLight 755 (Life Technologies); IRDye 800CW, IRDye 800RS, and IRDye 700DX (Li-Cor); VivoTag680, VivoTag-S680, and VivoTag-S750 (PerkinElmer).

An "enzyme moiety" refers to polypeptides that catalyze the production of a detectable signal. Exemplary enzyme moieties may include, without limitation, horseradish peroxidase (HRP), alkaline phosphatase (AP), glucose oxidase, or β-galactosidase.

"Optical moieties" may include, for example, any agents that may be used to produce contrast or signal using optical imaging such as luminescence or acousto-optical moieties.

"Magnetic moieties" may include, for example, a chelating agent for magnetic resonance agents. Chelators for magnetic resonance agents can be selected to form stable complexes with paramagnetic metal ions, such as Gd(III), Dy(III), Fe(III), and Mn(II).

Other exemplary detectable imaging agents may include radiolabel moieties. Exemplary radioactive labels may include, without limitation, $^{99}$Mo, $^{99m}$Tc, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{n}$C, $^{x}$3N, $^{15}$O, and $^{18}$F.

"X-ray moieties" may include, for example, any agents that may be used to produce contrast or signal using X-ray imaging such as iodinated organic molecules or chelates of heavy metal ions.

Ultrasound imaging moieties may include, for example, any agents that may be used to produce contrast or signal using ultrasound imaging such as Levovist, Albunex, or Echovist.

A detectable imaging agent may also be a nanoparticle-based moiety. A nanoparticle-based moiety is a nanoparticle that is capable of generating a signal. For example, silicon containing nanoparticles may be used to produce fluorescence, luminescence, or another type of signal. Other exemplary nanoparticle-based moieties include, without limitation, nanospheres such as Kodak X-SIGHT 650, Kodak X-SIGHT 691, Kodak X-SIGHT 751 (Fisher Scientific); metal oxide nanoparticles; and quantum dots such as Evi-Tags (Evident Technologies) or Qdot probes (Life Technologies). Nanoparticles may also be used to link or conjugate the antigen-binding reagents to a toxin or other cytotoxic agent or cytotoxic compound.

A "therapeutic agent" may be any substance that provides a therapeutic functionality when conjugated to an antigen-binding reagent. For example, antibody-drug conjugates including the antigen-binding reagents disclosed herein are contemplated. Suitable therapeutic agents may include, without limitation, cytotoxic compounds, and particularly those shown to be effective in other antibody-drug conjugates. As used herein, a "cytotoxic compound" refers to any substance that disrupts the functioning of cells and/or causes the death of cells. Various therapeutic cytotoxic compounds are known in the art and may include, without limitation, DNA damaging agents, anti-metabolites, natural products and their analogs. Exemplary classes of cytotoxic compounds include enzyme inhibitors such as dihydrofolate reductase inhibitors, and thymidylate synthase inhibitors, tubulin inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, auristatins, maytansinoids, differentiation inducers, and taxols.

More specifically, suitable cytoxic compounds may include 5-fluorouracil, aclacinomycin, activated cytoxan, bisantrene, bleomycin, carmofur, CCNU, cis-platinum, daunorubicin, doxorubicin, DTIC, melphalan, methotrexate, mithramycin, mitomycin, mitomycin C, peplomycin pipobroman, plicamycin, procarbazine, retinoic acid, tamoxifen, taxol, tegafur, VP16, VM25, diphtheria toxin, botulinum toxin, geldanamycin, maytansinoids (including DM1), monomethylauristatin E (MMAE), monomethylauristatin F (MMAF), and maytansinoids (DM4) and their analogues.

Exemplary cyotoxic compounds may also include therapeutic radiopharmaceuticals including, without limitation, $^{186}$Re, $^{188}$Re, $^{153}$Sm, $^{67}$Cu, $^{105}$Rh, $^{m}$Ag, and $^{192}$Ir.

In one embodiment the antigen-binding reagents may be used to initiate antibody-dependent cellular cytotoxicity (ADCC) and may thus be used to kill the cancer cells. The ADCC data in the examples demonstrates that when the scFvC9 is linked to full length IgG (such as the anti-cmyc used int eh Examples), it can initiate an effective ADCC response. The V5 tag antibody described herein may perform similarly.

Preparation of antibody-drug conjugates is generally known in the art and can be performed by conventional methods analogous to those described in, for example, Doronina et al., Bioconjugate Chem. 2006, 17, 114-124. See also for example U.S. Pat. Nos. 8,067,546, 8,039,273, 7,989,434, 7,851,437, 7,837,980, 7,829,531, 7,705,045 8,034,959, 8,034,787, 7,968,586, 7,847,105, and 7,223,837.

An "immunopolypeptide" may be any polypeptide that facilitates an immune function. For example, the antigen-binding reagents disclosed herein may be combined with further immunopolypeptides to produce new chimeric antigen receptors (CARs) specific for Periostin. CARs may include a targeting moiety such as any of the antigen-binding reagents disclosed herein, and additional "immunopolypeptides" such as a transmembrane domain, and intracellular signaling/activation domain(s). Intracellular signaling/activation domain(s) suitable as immunopolypeptides include, without limitation, CD3 signaling domains, 41BB-signaling domains, CD28-signaling domains, or combinations thereof. The immunopolypeptide may also be immunoglobulin domains important in developing dendritic based vaccines.

The antigen-binding reagent and agent may be linked directly by a covalent bond or may be linked using a linker or spacer moiety. Useful linker or spacer moieties include peptides, amino acids, nucleic acids, as well as homofunctional linkers or heterofunctional linkers. Particularly useful conjugation reagents that can facilitate formation of a covalent bond between an antigen-binding reagent and agent may include a N-hydroxysuccinimide (NHS) ester and/or a maleimide. In some embodiments, the antigen-binding reagent and agent are linked at the N-terminal end of the antigen-binding reagent. In some embodiments, the antigen-binding reagent and are linked at the C-terminal end of the antigen-binding reagent. In some embodiments, the linker is at least 2, 3, 4, 5, 6, 7, 8, or more amino acids long.

In embodiments covering antibody-drug conjugates, the linker may be cleavable under intracellular or extracellular conditions, such that cleavage of the linker releases the therapeutic agent from the antigen-binding reagent in the appropriate environment. For example, the linker may be cleavable by extracellular or intracellular proteases including, without limitation, lysosomal or endosomal proteases. Suitable linkers cleavable by an intracellular protease may include a Val-Cit linker or a Phe-Lys linker. See, e.g., U.S. Pat. No. 6,214,345.

In some embodiments, the therapeutic agent may be released after degradation of the antigen-binding reagent and/or linker in, for example, lysosomes. See, e.g., U.S. Publication No. 2005/0238649.

The linker may be cleavable by a cleaving agent that is present in the intracellular environment (e.g., within a lysosome or endosome or caveolea).

In some embodiments, the linker may be cleavable by cathepsins B and D and plasmin, all of which are known to hydrolyze dipeptide drug derivatives resulting in the release of active drug inside target cells.

The linker may be pH-sensitive, for example, sensitive to hydrolysis at certain pH values. Typically, a pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, thioether, or the like) may be used. See, e.g., U.S. Pat. Nos. 5,122,368; 5,824,805; 5,622,929. Such linkers are relatively stable under neutral pH conditions, like in the blood, but are unstable at below pH 5.5, the approximate pH of the lysosome.

In some embodiments, the linker may be cleavable under reducing conditions (e.g., a disulfide linker). A variety of disulfide linkers are known in the art, including, for example, those that can be formed using SATA (N-succinimidyl-5-acetylthioacetate) and SPDB (N-succinimidyl-3-(2-pyridyldithio) butyrate).

In some embodiments, the linker is self-immolative. See, e.g., WO 2007059404A2, WO06110476A2, WO05112919A2, WO2010/062171, WO09/017394, WO07/089149, WO 07/018431, WO04/043493 and WO02/083180.

A variety of exemplary linkers that can be used with the present invention are described in WO 2004010957, U.S. Publication No. 2006/0074008, U.S. Publication No. 20050238649, and U.S. Publication No. 2006/0024317.

In some embodiments, the antigen-binding reagent and the agent are linked by a tag system. A tag system includes any group of agents capable of binding one another with a high affinity. Several tag systems are well-known in the art and include, without limitation, biotin/avidin, biotin/streptavidin, or digoxigenin (DIG) systems. In some embodiments, the tag system includes biotin/avidin or biotin/streptavidin. In such embodiments, the antigen-binding reagent may be modified at either the N-terminus or C-terminus to include biotin while the agent may be modified to include streptavidin or avidin. Alternatively, the antigen-binding reagent may be modified at either the N-terminus or C-terminus end to include streptavidin or avidin while the agent may be modified to include biotin.

Cells

In a further aspect of the present invention, cells are provided. The cells may include any one of the antigen-binding reagents or any one of the antigen-binding conjugates described herein. The cells may be mammalian cells such as, without limitation, human cells.

In some embodiments, the cells may be cancerous cells such as, without limitation, ovarian cancer cells or lung cancer cells.

In some embodiments, the cells may be immune cells such as, without limitation, T cells or Natural Killer (NK)

cells. For example, the immune cells may be engineered immune cells, such as T cells or NK cells, including the chimeric antigen receptors (CARs) described herein.

Pharmaceutical Compositions

In a still further aspect of the present invention, pharmaceutical compositions are provided. The pharmaceutical compositions may include any of the antigen-binding reagents, any of the antigen-binding conjugates, or any of the cells disclosed herein and a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

Methods

Various in vitro and in vivo diagnostic and/or therapeutic methods using the compositions disclosed herein are contemplated.

In a further aspect, the present invention relates to methods for imaging cancer cells in a subject. The methods may include administering in an effective amount any of the antigen-binding reagents, any of the antigen-binding conjugates, or any of the pharmaceutical compositions described herein to the subject, and generating an image of at least a portion of the subject using an imaging modality. Preferably in these method embodiments, the imaging of cells bound to the antigen-binding reagent, antigen-binding conjugate, or pharmaceutical composition is indicative of the cells being cancer cells.

As used herein, the term "subject" refers to both human and non-human animals. The term "non-human animals" of the disclosure includes all vertebrates, e.g., mammals and non-mammals, such as non-human primates, sheep, dog, cat, horse, cow, chickens, amphibians, reptiles, and the like. Suitably, the subject is a human patient.

As used herein, "imaging modality" may include any technology capable of generating an image of a subject. In some embodiments, the imaging modality may be selected from the group consisting of ultrasound, positron-emission tomography (PET), photon emission computed tomography (SPECT), nuclear magnetic resonance imaging (NMRI), optical imaging (OI) and computed tomography (CT). For example, in some embodiments of the present methods, the present inventors contemplate that some of the compositions disclosed herein may be used in conjunction with ultrasound technologies to image pelvic masses in a subject to determine whether such masses are benign or cancerous. Such diagnostic imaging methods would be useful prior to removal of the pelvic mass because the prognosis of the subject after removal of the pelvic mass is directly related to the type of surgeon that performs the surgery. If the imaging methods indicate that the pelvic mass is cancerous, the subject may be directed to a surgeon specializing in removing cancerous tissue. On the other hand, if the imaging methods indicate that the pelvic mass is benign, the subject may be directed to a general surgeon whom may remove the mass and may not have any particular experience in removing cancerous tissue. In some embodiments of such methods, antigen-binding conjugates disclosed herein including one or more ultrasound imaging moieties may be administered to the subject and then ultrasound images may be generated of the pelvic region of the subject using, for example, transvaginal or other ultrasound imaging technologies. If the ultrasound image shows significant detectable signal from the ultrasound imaging moiety in or around the pelvic mass this would indicate that the pelvic mass is cancerous.

In another aspect, the present invention relates to methods of detecting cancer cells in a subject sample. The methods may include obtaining a sample from the subject, contacting the sample with any of the antigen-binding reagents or any of the antigen-binding conjugates disclosed herein, and detecting binding of the antigen-binding reagent or antigen-binding conjugate to cells in the sample. Suitably, binding of the antigen-binding reagent or the antigen-binding conjugate to the cells is indicative of the cells being cancer cells. Alternatively, the methods may include administering an imaging or other detectable agent linked to the antigen-binding reagents provided herein to the subject and then detecting binding of the antigen-binding reagent or antigen-binding conjugate to cells in the subject. The ability of the antigen-binding reagent to bind cells in the subject and produce a detectable signal is indicative of the subject having cancer. The administration can be carried out by any means available to those skilled in the art and will vary depending on the type of cancer suspected.

The "sample" may include cells. In particular, the methods described herein may be performed without requiring a tissue sample or biopsy. "Sample" is intended to include any sampling of cells, tissues, or bodily fluids in which cancer cells may be detected. Examples of such samples include, without limitation, blood, serum, urine, synovial fluid, saliva, or any other bodily secretion or derivative thereof. Blood can include whole blood, plasma (citrate, EDTA, heparin), serum, or any derivative of blood. Samples may be obtained from a subject by a variety of techniques available to those skilled in the art. Methods for collecting various samples are well known in the art. In some embodiments, the sample is serum or plasma.

As used herein, "contacting" may be carried out through any of the variety of procedures used to apply compositions to samples that will be apparent to the skilled artisan including, without limitation, simple addition of the composition to the sample.

Methods suitable for "detecting" the binding of the antigen-binding reagent or antigen-binding conjugate to cells in the sample are known to those of skill in the art and may include, without limitation, ELISA, immunofluorescence, FACS analysis, Western blot, magnetic immunoassays, and antibody-based microarrays. In the past, the gold standard for detection of cells in blood was the use of ELISAs; however, liquid biopsy technologies offer an attractive alternative approach for cellular analysis.

In a further aspect, the present invention relates to methods of treating cancer cells in a subject. The methods may include administering to the subject an effective amount any of the antigen-binding reagents, any of the antigen-binding conjugates, any of the cells, or any of the pharmaceutical compositions disclosed herein to treat the cancer in the subject. The cancer and cancer cells include cancers and cancer cells with increased expression of the Mgat3 gene. These cancers include, but are not limited to, ovarian, lung, glioblastoma, kidney clear cell, uterine corpus endometrioid, rectum adenocarcinoma, colon, and adenocarcinoma. In lung cancers lung squamous cell and lung adenocarcinoma are reported to have increased Mgat3 expression and thus would be candidates for the methods provided herein. Several cancers have been identified (see ref. 23) and the inventors expect additional cancers will be identified that have epigenetic hypomethylation changes to Mgat3.

Treating cancer cells includes, without limitation, reducing the number of cancer cells or the size of a tumor in the subject, reducing progression of a cancer to a more aggressive form, reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

In some embodiments of the present methods, the methods may further include administering an effective amount of an anti-cancer therapeutic agent to the subject.

The "anti-cancer therapeutic agent" may be any therapeutic agent that is used to treat cancer in a subject. Suitable anti-cancer therapeutic agents may include, without limitation, radiation, chemotherapy agents, anti-cancer biologics, or immunotherapy agents. Chemotherapy agents are chemotherapeutic compounds that may be used to treat cancer. Suitable chemotherapy agents may include, without limitation, 5-fluorouracil, aclacinomycin, activated cytoxan, bisantrene, bleomycin, carmofur, CCNU, cis-platinum, daunorubicin, doxorubicin, DTIC, melphalan, methotrexate, mithramycin, mitomycin, mitomycin C, peplomycin pipobroman, plicamycin, procarbazine, retinoic acid, tamoxifen, taxol, tegafur, VP16, or VM25.

Anti-cancer biologics are biomolecules (e.g., polynucleotides, polypeptides, lipids, or carbohydrates) that may be used to treat cancer. Anti-cancer biologics may include, without limitation, hormones, cytokines such as IL-1α, IL-2, IL-2β, IL-3, IL-4, CTLA-2, IFN-α, IFN-γ, granulocyte-macrophage colony stimulating factor (GM-CSF), IL-12, IL-23, IL-15, IL-7, or any combination thereof; or anti-cancer antibodies such as Rituximab, Trastuzumab, Gemtuzumab, Alemtuzumab, Ibritumomab tiuxetan, Tositumomab, Cetuximab, Bevacizumab, Panitumumab, Ofatumumab, Brentuximab Vedotin, Pertuzumab, Ado-trastuzumab emtansine, and Obinutuzumab.

The term "immunotherapy agent(s)" refers to any therapeutic that is used to treat cancer in a subject by inducing and/or enhancing an immune response in that subject. Immunotherapy agents may include, without limitation, checkpoint inhibitors, cancer vaccines, immune cells such as engineered T cells, anti-cancer viruses, or bispecific antibodies.

Checkpoint inhibitors are therapeutics, such as antibodies, that block the immune checkpoint pathways in immune cells that are responsible for maintaining self-tolerance and modulating the degree of an immune response. Tumors often exploit certain immune checkpoint pathways as a major mechanism of immune resistance against T cells that are specific for tumor antigens. Many of the immune checkpoints are initiated by receptor-ligand interactions and thus may be blocked by antibodies to either the ligand or receptor or may be modulated by soluble recombinant forms of the ligands or receptors. Such immune checkpoint blockade allows tumor-specific T cells to continue to function in an otherwise immunosuppressive tumor microenvironment. Exemplary checkpoint inhibitors include, without limitation, antibodies or other therapeutics targeting programmed cell death protein 1 (PD1, also known as CD279), programmed cell death 1 ligand 1 (PD-L1, also known as CD274), PD-L2, cytotoxic T-lymphocyte antigen 4 (CTLA4, also known as CD152), A2AR, CD27, CD28, CD40, CD80, CD86, CD122, CD137, OX40, GITR, ICOS, TIM-3, LAG3, B7-H3, B7-H4, BTLA, IDO, KIR, or VISTA. Suitable anti-PD1 antibodies include, without limitation, lambrolizumab (Merck MK-3475), nivolumab (Bristol-Myers Squibb BMS-936558), AMP-224 (Merck), and pidilizumab (CureTech CT-011). Suitable anti-PD-L1 antibodies include, without limitation, MDX-1105 (Medarex), MEDI4736 (Medimmune) MPDL3280A (Genentech/Roche) and BMS-936559 (Bristol-Myers Squibb). Exemplary anti-CTLA4 antibodies include, without limitation, ipilimumab (Bristol-Myers Squibb) and tremelimumab (Pfizer).

Cancer vaccines stimulate the body's immune system to attack cancer cells. Cancer vaccines generally include a tumor antigen in an immunogenic formulation that activates tumor antigen-specific helper T cells and/or cytotoxic T cells and B cells. Vaccines can be in a variety of formulations, including, without limitation, dendritic cells, monocytes, viral, liposomal and DNA vaccines. Suitably, the dendritic cells are autologous and transfected with tumor cells or tumor antigens. Dendritic cells are immune cells that present antigens to T cells, which prompted their application in therapeutic cancer vaccines. Following the loading of dendritic cells with tumor antigens ex vivo, the dendritic cells may be administered as a cellular vaccine which has been found to induce protective and therapeutic anti-tumor immunity. Exemplary cancer vaccines include, without limitation, Sipuleucel-T (Provenge®, or APC8015). Sipuleucel-T is an FDA-approved cancer vaccine developed from autologous dendritic cells (DC) loaded with engineered fusion protein of prostatic acid phosphatase (PAP) and granulocyte-macrophage colony-stimulating factor (GM-CSF).

An immunotherapy agent may include immune cells (i.e., T cells or B cells) that are adoptively transferred into a subject to attack or reduce cancer cells or cancer cell growth. The immune cells may be autologous or derived from a subject that is different from the subject receiving the immune cells and modified to reduce rejection. The immune cells may also have a natural or genetically engineered reactivity to a subject's cancer. For example, natural autologous T cells have been shown to be effective in treating metastatic cancers. See, e.g., Rosenberg S A et al., *Nat. Rev. Cancer* 8 (4): 299-308 (2008). Natural autologous T cells may be found within a resected subject's tumor. Such T cells can be induced to multiply in vitro using high concentrations of IL-2, anti-CD3 and allo-reactive feeder cells. These T cells are then transferred back into the subject along with, for example, exogenous administration of IL-2 to further boost their anti-cancer activity.

The T cells may also include engineered T cells. Engineered T cells are T cells that have been genetically modified so as to direct T cells to specifically destroy a subject's cancer cells. Engineered T cells may, for example, include T cells that have been genetically modified to express chimeric antigen receptor (CAR) proteins or "CAR T cells."

An immunotherapy agent may include an oncolytic virus. As used herein, an "oncolytic virus" refers to any virus that may be used to treat cancer. Exemplary oncolytic viruses include, without limitation, PVS-RIPO, T-VEC, and Onyx-015. PVS-RIPO is a genetically modified oral poliovirus that has been fast-tracked by the FDA for the treatment of recurrent glioblastoma multiforme (GBM). T-VEC (Imlygic) is an FDA-approved oncolytic virus for the treatment of melanoma in patients with inoperable tumors. Onyx-015 is an oncolytic adenovirus.

Bispecific antibodies may also be used as an immunotherapy agent in accordance with the present invention. A bispecific antibody is an antibody having binding sites for a tumor-associated antigen and for a T-cell surface receptor that can direct the lysis of specific tumor cells by T cells. Bispecific antibodies have been used, for example, to successfully treat brain tumors in human patients. See, e.g., Nitta et al., *Lancet* 355:368-371 (1990). Numerous methods to produce bispecific antibodies are known in art including, without limitation, the quadroma method (See, e.g., Milstein and Cuello, *Nature,* 305:537-540 (1983)), use of heterobifunctional cross-linkers to chemically tether two different antibodies or antibody fragments (See, e.g., Staerz et al., Nature 314:628-631 (1985); European Patent Application 0453082), or DOCK-AND-LOCK methods (See, e.g., U.S. Pat. Nos. 7,550,143; 7,521,056; 7,534,866; 7,527,787 and 7,666,400).

A bispecific antibody may include a trifunctional antibody that includes two heavy and two light chains, one each from two different antibodies. The two Fab regions are directed against two antigens while the Fc region is made up from the two heavy chains and forms the third binding site, which typically may elicit effector functions. A bispecific antibody may include chemically linked Fab regions, various types of bivalent and trivalent single-chain variable fragments (scFvs), or fusion proteins mimicking the variable domains of two antibodies. Suitable bispecific antibodies include, without limitation, Removab (Trion Pharma), Blincyto (Amgen), AMG-110 (Amgen), ABT-122 (Abbvie), ABT-981 (Abbvie), AFM13 (Affimed Therapeutics), MM-111 (Merrimack Pharmaceuticals), SAR156597 (Sanofi), RG7221 (Roche), RG6013 (Roche), RG7597 (Roche), ALX-0761 (Ablynx), MCLA-128 (Merus), MEDI-565 (AMG-211), MGD006 (Macrogenics), and REGN1979 (Regeneron).

An "effective amount" or a "therapeutically effective amount" as used herein means the amount of a composition (e.g. antigen-binding reagents, antigen-binding conjugates, cells, pharmaceutical compositions or anti-cancer therapeutic agents) that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

In accordance with the present methods, the compositions (e.g., antigen-binding reagents, antigen-binding conjugates, cells, or anti-cancer therapeutic agents) and pharmaceutical compositions described herein may be "administered" by any means known to those skilled in the art, including, without limitation, intravenously, intra-tumoral, intra-lesional, intradermal, topical, intraperitoneal, intramuscular, parenteral, subcutaneous and topical administration Thus the compositions may be formulated as an injectable, topical or ingestible, suppository formulation. Administration of the compositions and pharmaceutical compositions to a subject in accordance with the present invention may exhibit beneficial effects (e.g., therapeutically or diagnostically) in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage of a composition (e.g. antigen-binding reagents, antigen-binding conjugates, cells, pharmaceutical compositions or anti-cancer therapeutic agents) administered in any given case will be adjusted in accordance with the composition or compositions being administered, the volume of the composition that can be effectively delivered to the site of administration, the disease to be treated or inhibited, the condition of the subject, and other relevant medical factors that may modify the activity of the compositions or the response of the subject, as is well known by those skilled in the art. For example, the specific dose of a composition (e.g. antigen-binding reagents, antigen-binding conjugates, cells, pharmaceutical compositions or anti-cancer therapeutic agents) for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol. The compositions can be given in a single dose schedule, or in a multiple dose schedule.

The maximal dosage of a (e.g. antigen-binding reagents, antigen-binding conjugates, cells, pharmaceutical compositions or anti-cancer therapeutic agents) for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will treat cancer by, for example, by reducing tumor size or decreasing the rate of tumor growth by least 10%, 20%, 30%, 40%, 50%, 60%, 70%, 80%, 90%, 100% or more as compared to no treatment.

The effective dosage amounts of a (e.g. antigen-binding reagents, antigen-binding conjugates, cells, pharmaceutical compositions or anti-cancer therapeutic agents) herein refer to total amounts administered, that is, if more than one composition is administered, the effective dosage amounts of a composition corresponds to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The compositions (e.g. antigen-binding reagents, antigen-binding conjugates, cells, pharmaceutical compositions or anti-cancer therapeutic agents) described herein may be administered one time or more than one time to the subject to effectively treat cancer. Suitable dosage ranges for a composition may be of the order of several hundred micrograms of the inhibitor and/or agent with a range from about 0.001 to 10 mg/kg/day, preferably in the range from about 0.01 to 1 mg/kg/day. Precise amounts of a composition required to be administered depend on the judgment of the practitioner and may be peculiar to each subject. It will be apparent to those of skill in the art that the therapeutically effective amount of the compositions and pharmaceutical compositions described herein will depend, inter alia, upon the administration schedule, the unit dose of agent administered, whether the composition is administered in combination with other therapeutic agents, the status and health of the recipient, and the therapeutic activity of the particular composition.

The effectiveness of an anti-cancer therapeutic agent may be enhanced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% when combined with a composition (e.g. antigen-binding reagents, antigen-binding conjugates, cells, pharmaceutical compositions) disclosed herein and relative to a control treated with the anti-cancer therapeutic agent alone. Suitably, the compositions and methods described herein may reduce the size of a tumor or the spread of a tumor in a subject by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as saline or relative to administration of the anti-cancer therapeutic agent alone.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Selection and Characterization of a Novel scFv Antibody that Targets Tumor-Specific N-Linked Glycans Materials and Methods Cell Lines Periostin cDNA cloned into a retroviral vector was a gift from Dr. Xiao-Fan Wang (Duke University, Durham, NC). Virus was produced using 293-GP2 packaging cells and the VSV-G envelope prior to transduction into recipient cells (Lec4, Pro5, OVCAR3) to create periostin (PN) expressing cell lines used for depletions and enrichments. The CHO cell lines Lec4 and Pro5 were gifts from Dr. Pamela Stanley (Albert Einstein College of Medicine, Bronx, NY). The OVCAR3 and OVCA26 control and GnT-III shRNA cell lines have previously been described[3,29]. Human mesothelin A1847, C30, and human mesothelin Luc-ID8 cell lines were generated by Dr. Scholler (SRI International, Menlo Park, CA).

Western Blot Analysis

Cell culture supernatant (50 mL) was collected from OVCAR3-PN, Pro5-PN, and Lec4-PN cells with the addition of protease inhibitors. Periostin was purified on anti-Flag resin (Sigma-Aldrich) according to the manufacturer instructions. Proteins were separated on NuPage 4-12% BisTris gel using 1×MES buffer prior to transfer to PVDF membrane. Blots were blocked in 3% BSA/1×TBST before detection of bisecting glycans using (1:5,000) dilution of biotin labeled E-PHA (Vector Labs) and (1:10,000) dilution of streptavidin HRP (Vector Labs) followed by enhanced chemiluminescent detection. The blot was stripped in Pierce (Thermo) stripping buffer, blocked in 5% nonfat milk 1×TBST and detected using (1:250) dilution of antibody to periostin (Santa Cruz Biotechnologies).

Selection of Bisecting Glycan-Selective scFv by Screening a Yeast-Display scFv Library A yeast display library of scFvs isolated from infiltrating B cells and PBMCs derived from 11 ovarian cancer patients has been previously described[30]. This library was grown in SD-CAA (0.67% yeast nitrogen base, and 0.5% Casamino acids) and the induction of cell surface display of scFv was induced as previously described[31]. Multiple rounds of library depletion were performed as follows: $1\times10^8$ induced yeast-display scFv in phosphate buffered saline (PBS) were added to PBS rinsed adherent Lec4-PN cells (95% confluent T175 flask). Non-adherent yeast after 30 min of incubation were taken to another T175 flask of Lec4-PN cells and this process was repeated for a total of 6 flasks. This process was repeated using Pro5-PN flasks. Next, this new depleted sub-library was grown and induced again and used to enrich for scFv binding to the tumor-specific glycosylation on periostin using the OVCAR3-PN cells. Following 6 rounds of enrichment with manual selection of bound yeast using a cell selector probe the level of enrichment was monitored using yeast-cell ELISA as follows: Yeast in the scFv enriched pool were spread on SD-CAA plates and allowed to grow for 2-3 days to allow colonies to develop. Individual colonies were streaked onto separate SD-CAA plates and induced with SGR-CAA to allow scFv expression on the yeast cell surface. Yeast scFv were labeled using fluorescent brightener 28 (Sigma-Aldrich, calcofluor) 1 mg/mL in $H_2O$/NaOH. Briefly, yeast with scFv on the cell surface were resuspended at $1\times10^7$ in calcofluor solution (10% final) for 5 min at room temperature followed by washes in PBS. Labeled yeast were panned on Lec4-PN/Pro5-PN/OVCAR3-PN cells at 90% confluence on 24-well plates for 30 min at room temperature. Differential yeast binding to cells were measured with an Envision 2104 multilabel reader at (Ex355/Em405) before and after each 5 minutes wash with gentle shaking. Post wash readings were made following removal of wash buffer and addition of fresh PBS.

Transformation of Yeast-Display scFv into Soluble scFv

ScFv DNA was PCR amplified from lysed yeast. Briefly, 5 μL of yeast grown at saturation were suspended in 20 μL of 20 mM NaOH and microwaved 3 min, to lyse yeast. DNA corresponding to the scFv fragment was amplified by PCR using Phire DNA polymerase and gel purified prior to cotransformation with linearized p416BCCP vector into the VYH10 yeast strain by electroporation[17]. Yeast were grown overnight in SD CAA media supplemented with tryptophan (TRP) and further induced in 1 mL of SGR CAA/TRP as previously described[6]. Soluble scFv were confirmed using an ELISA assay using the HIS and V5 tags for detection. Soluble scFv clones were transformed into site-specific biotinylated soluble antibodies (biobodies) as described previously[32].

ADCC Assay

OVCAR5 cells (3 wells per condition) were plated at $0.8\times10^4$ cells/well 48 hrs prior to addition of scFvC9 antibody alone, anti-myc antibody alone, or serial dilutions of scFvC9 mixed with anti-myc antibody. Complexes with scFvC9 at 0.5 mg/mL and anti-myc antibody at 1 mg/mL were formed at 4° C. for 30 min. prior to addition to cells. Serial dilutions of complexes and control scFvC9 alone (0.5 mg/mL or anti-myc antibody alone (1 mg/mL) were added to cells for 48 hrs. Equal volume of CellTiter-Glo Reagent (Promega) was added to each well. The plate was shaken on an orbital shaker for 2 minutes and placed at room temperature for 10 minutes prior to recording luminescence. The resulting cell lysis generates luminescent signal proportional to ATP present in the number of viable cells. Three independent experiments were performed.

Immunochemistry Cell Staining

Ovarian cancer cells were plated on poly L-lysine coverslips and grown to 50% confluence prior to immunofluorescent staining. scFvC9 biobody antibody (50 μg/mL) in PBS was added to cells for 5 min. or 30 min. time points. Cells were washed with PBS before fixation in ice cold methanol for 5 min. Cells were blocked with PBS/1% BSA for 10 min. before detection of scFvC9 biobody using streptavidin conjugated Alexa Fluor 594. Nuclei were counterstained with a 1:10,000 solution of DAPI for 10 seconds before mounting in Vectashield media.

Xenograft scFvC9 Imaging

Immune compromised NSG female mice were injected subcutaneously with $1.0\times10^6$ A1847 human ovarian cancer cells six wk before imaging studies. Immune competent C57Bl/6 female mice were injected intraovary or intraperitoneal with $1.0\times10^6$ luciferase transduced ID8 murine ovarian cancer cells 8 wk prior to imaging[33]. Luc-ID8 tumors were monitored with luciferin injections prior to the imaging study. Mice were anesthetized with isoflurane and imaged prior to antibody injection for baseline and then at the 2 min., 5 min., 30 min., 60 min., 4 hr, 24 hr, and 48 hr time points after injection of antibody complexes. The scFvC9 complexes included 30 μg scFvC9 biobody pre-incubated with 1:1 fluorescently labeled streptavidin IRB680W for 30 min at 4° C. to form complexes. IV injection of complexes was performed retro orbitally for all mice.

Immunofluorescence Localization of scFvC9 in Tissues

NSG mice bearing subcutaneous A1847 tumors were injected with 30 μg scFvC9 biobody and sacrificed 24 hr later to harvest tumor, kidney, spleen, lung, and liver. All tissues were immediately fixed in formalin and stored in 70% ethanol until tissue section. Slides were deparaffinized by sequentially dipping in xylene and grated ethanol series. Tissue was incubated with Streptavidin-Qdot 800 (diluted 1:50) in PBS for 1 hr at room temperature in the dark. Slides were washed 3 times in PBS/0.05% tween 20 and counterstain was performed with DAPI at 1:10,000 for 15 min. Slides were washed 2× in PBS and fluorsave reagent was used to mount the slides.

Magnetic Resonance Imaging

In Vitro Analysis—MRI imaging was performed on a 1.5 T MR system (Bruker PharmaScan 70/16). Phantom tubes were generated with A1847, C30, or ID8 cells ($0.4$-$1\times10^6$ cells) layered between spacers of agarose gel before or after incubation with 25 μg/mL or 50 μg/mL of scFvC9 coupled to anti-flag magnetic beads. The scFvC9/magnetic bead complexes were incubated with the cells for 30 min at 4° C. before washing and fixing with 2% paraformaldehyde for 20 minutes at 4° C. Fixed cells and scFvC9/magnetic complexes were then resuspended in 100 μL in 1% agarose gel and finally layered between spacers of 2% ultralow gel temperature agarose to generate phantom tubes. Optimal T1 and T2 weighted sequences were determined and regions of interest for each cell layer were measured for control cells only and control magnetic beads only for comparison with cells incubated with C9/magnetic beads. Results from three separate experiments were calculated and the ±SEM for normalized signal intensities were calculated.

In Vivo Analysis—MRI imaging was performed on a 1.5T MR system. NSG mice bearing 6 wk subcutaneous A1847 xenograft tumors were injected with avidin-coated magnetic beads only or scFvC9 biobody coupled 1:2 with avidin-coated magnetic beads in 100 μL of PBS for 30 minutes at 4° C. Regions of interest were calculated for tumor and control (muscle) across each 2 mm slice. The temperature during MR imaging was 28° C. and the time of acquisition was 30 min. Signal intensity (SI) values of tumor were divided by control (muscle) to yield the normalized signal intensity. Normalized signal intensities were calculated before and 1 hr, 4 hr, or 24 hr following magnetic bead only or C9/magnetic bead injections via retro orbital injection.

Animal Study Ethics

All animal studies and procedures were conducted under a protocol approved by the SRI International Institutional Animal Care and Use Committee. All methods were performed in accordance to guidelines and regulations at SRI International. SRI International maintains a centralized animal care and use program registered with the U.S. Department of Agriculture (USDA), accredited by the Association for Assessment and Accreditation of Laboratory Animal Care International (AAALAC) and has an assurance on file with the Office of Laboratory Animal Welfare (OLAW).

Results

Selection of Human scFvs Binding with Tumor-Specific Glycans

Periostin has one highly conserved N-linked glycosylation site located in the last FAS1 domain near the C-terminus of the protein (FIG. 1A). The functions of the glycosylation present on periostin are not known; however, this site is highly conserved in sequence implying its potential importance, and this site is present in all known isoforms of periostin. The conservation and location of the N-glycosylation site in an unstructured, solvent exposed region[34,35] (FIG. 1B) led us to the hypothesis that we could use the perostin protein as a scaffold to display different glycoforms of periostin allowing subtraction and enrichment of specific scFv antibodies to glycoforms of periostin. The top image displays the NMR structure of the last FAS1 domain of human periostin (FIG. 1B) indicates that asparagine 599 (the amino acid that is glycosylated) is located in the unstructured loop. The location of this region within the crystal structure of all FAS1 domains is shown in the bottom image further validating the exposure of the N-glycosylation site. There are three main forms of N-glycans: high mannose-type, hybrid-type, or complex-type. Typical glycoproteins have several N-glycosylation sites that can consist of any of these three forms. It is not yet well understood why certain sites have a tendency to be high mannose and other sites are hybrid or complex. However, prior research studies indicate there is site specificity for these glycan forms within glycoproteins[36]. We have determined that the single N-glycosylation site in periostin displays complex N-glycans due to the glycosylation pattern changes in different cancers. Our previous glycoproteomic analysis of breast cancer tissues indicates that periostin displays tetra-antennary sialylated complex N-linked glycans[37]. In ovarian cancer tissues our previous studies indicate that periostin displays truncated, agalactosylated, asialylated N-glycan structures with or without core fucose[3,24]. Despite the high expression in human cancer tissues, human cancer cell lines grown under adherent growth conditions do not express periostin. Cell lines that are grown under non-adherent conditions permit the formation of spheroids that begin to express periostin. We created stable periostin expression in the ovarian cancer cell line OVCAR3 as well as the non-malignant Chinese hamster ovary (CHO) cell lines Pro5 (parental) and Lec4 (lacking GnT-V expression) to allow expression under adherent growth conditions. As shown in FIG. 1C, periostin isolated using a Flag tag antibody bound to the lectin E-PHA, a lectin known to recognize bisecting N-glycans[38], only for the OVCAR3-PN cell line indicating the presence of bisecting glycans. There are additional higher molecular weight bands reacting bound by E-PHA indicating that other glycoproteins were isolated with periostin that also carry this form of glycosylation in ovarian cancer cells. The Pro5-PN and Lec4-PN flag tag pull downs are negative for E-PHA binding reflecting an absence of bisecting glycosylation in these cell lines (FIG. 1C). Previously published mass spectrometry analysis of N-glycosylated glycoforms found on glycoproteins isolated from Pro5 and Lec4 cells lines suggests that tetra-antennary and tri-antennary complex-type N-glycans are prominent in these cell lines[39]. All cell lines express similar levels of periostin protein (FIG. 1C). These results confirm that periostin is expressed in these cell lines with different forms of complex-type N-glycans enabling us to use these for the subtraction and selection of scFv antibodies.

Figure 3:
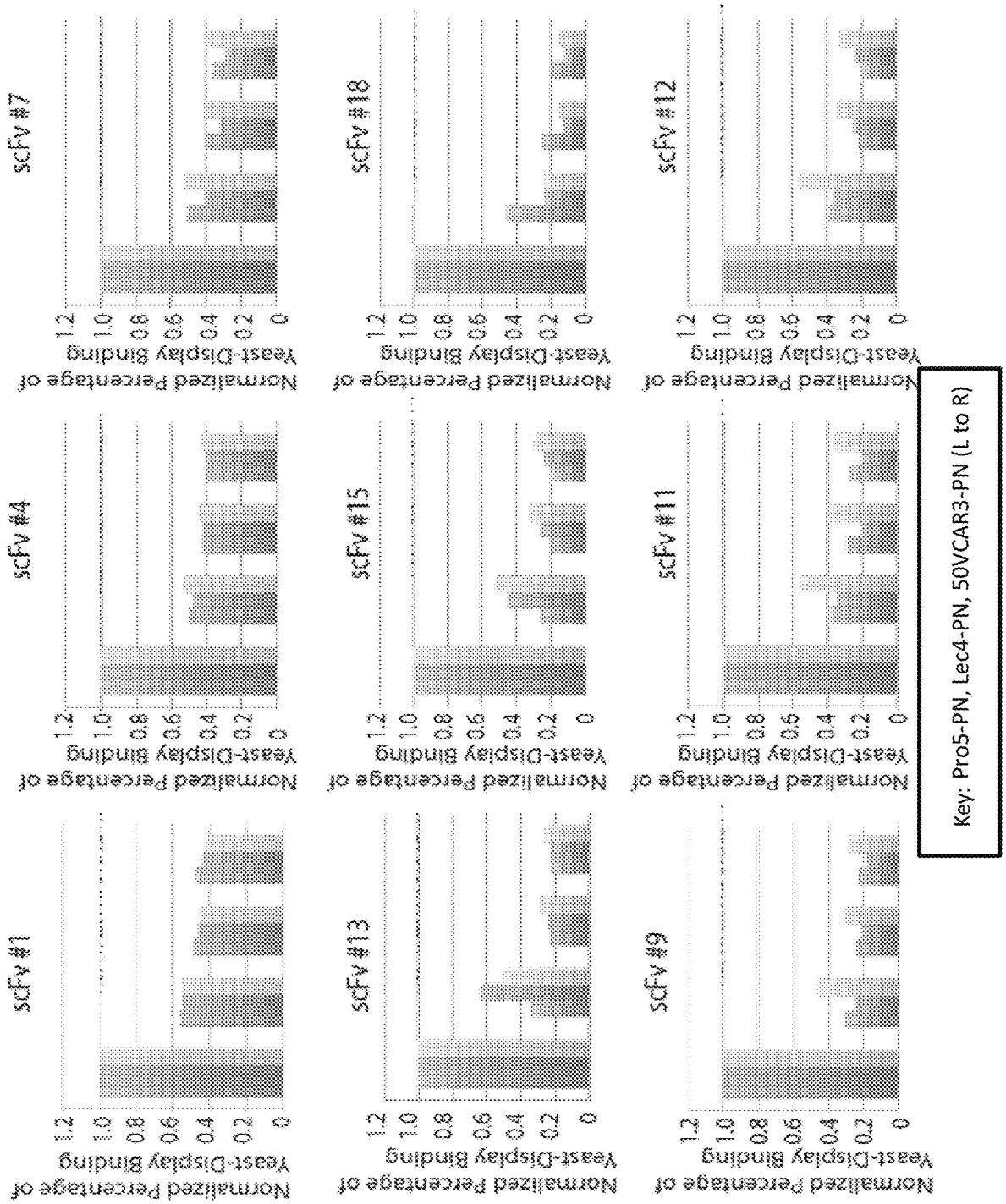
FIG. 3 shows representative yeast-cell ELISA results. Differential binding of candidate clonal yeast populations were measured on Pro5-PN, Lec4-PN, and OVCAR3-PN cells (grouped left to right in each graph) plated at 90% confluence on 24-well plates. Bound yeast (labeled with Calcofluor) were measured before and after washes. Representative data shown reflect the percentage of yeast bound after each wash for each cell line for the indicated clones.

The scFv yeast-display library used was isolated from the B cells of ovarian cancer patients. Our enrichment strategy described in FIG. 2 consists of multiple rounds of subtraction using the Pro5-PN and Lec4-PN cell lines to create a new sub-library that is then added to OVCAR3-PN cells to select binding yeast clones. Yeast-display binding clonal populations (n=21) were further screened by panning onto adherent OVCAR3-PN, Lec4-PN, and Pro5-PN cells using a yeast cell-ELISA procedure. FIG. 3 shows a representative analysis of scFv binding clones using these cell lines. Certain clones such as #1, #4, and #7 bound with similar affinity to all cell lines following sequential washes suggesting that these clones do not demonstrate specificity and affinity for any cell line; other clones such as #13, #15, and #18 bound best to Lec4-PN and OVCAR3-PN (#13 and #15) or Pro5-PN (#18) indicating these scFv clones show affinity to protein elements or glycan elements that are not ovarian cancer specific. However, other clones such as #9, #11, and #12 differentially bound with affinity to OVCAR3-PN cells following each sequential wash indicating specificity for ovarian cancer. Clone #9, #11, and #12 were transformed into soluble scFv antibody as previously described[17].

Figure 4A:
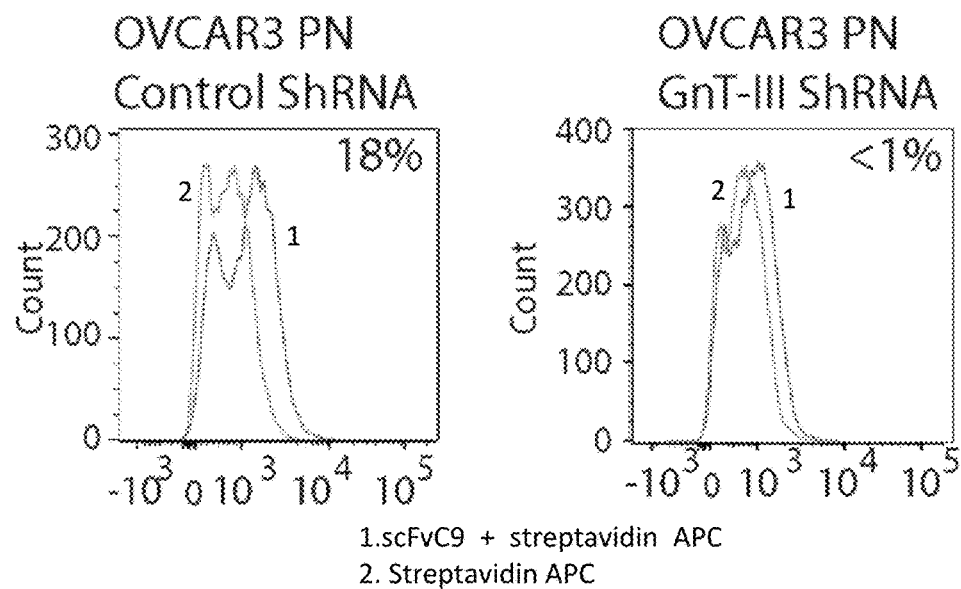
Figure 4B:
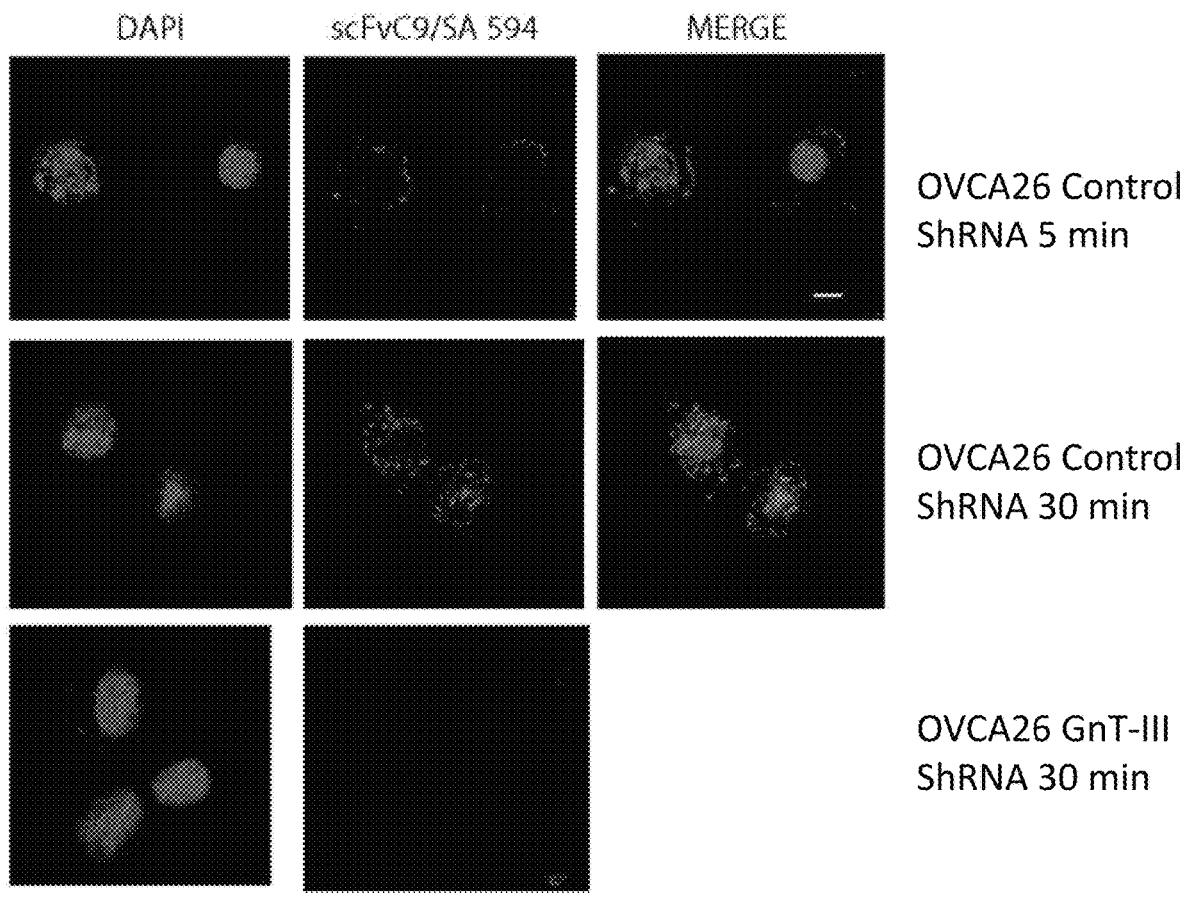
Figure 4D:
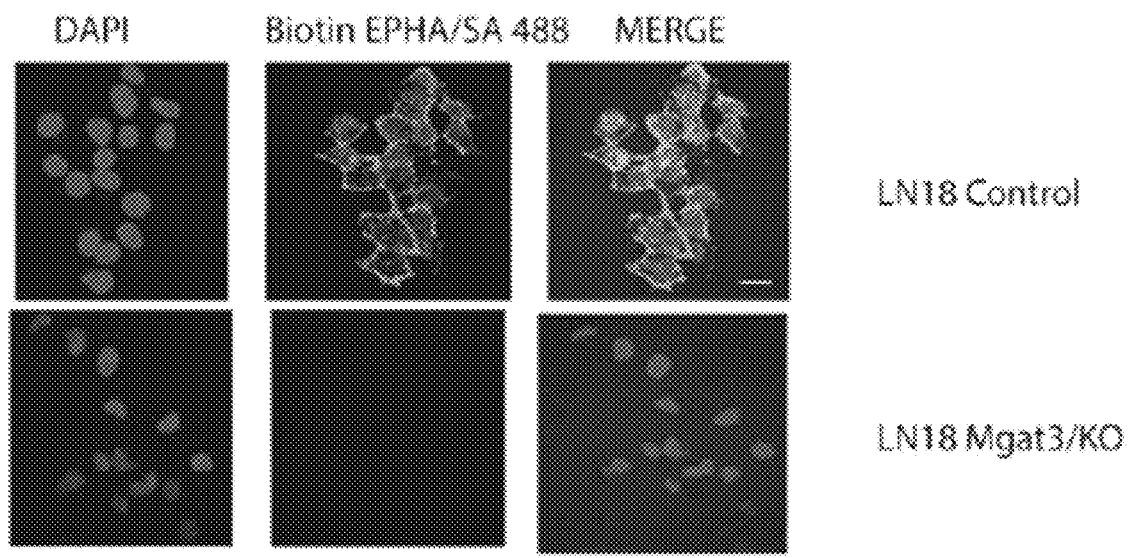
Figure 4E:
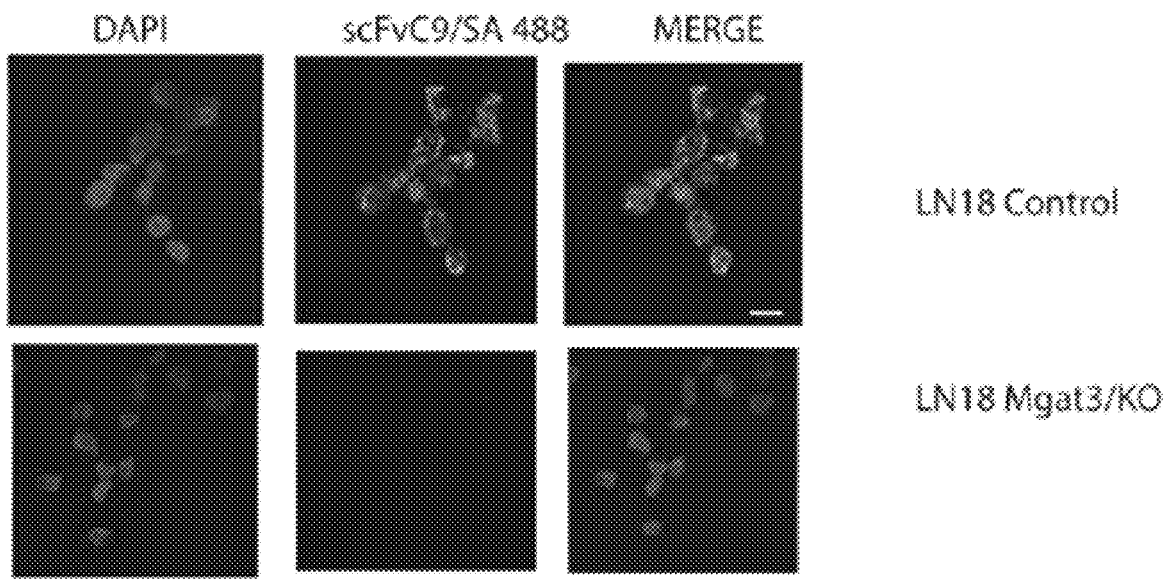

In Vitro Analysis of scFvC9 Binding Specificity, Distribution, and Antibody-Initiated Cytotoxicity Clone #9 had the optimal yields of soluble biotin labeled scFv antibody production and was further analyzed for binding specificity to bisecting N-glycans using OVCAR3 cells. We established stable periostin expression in OVCAR3 cells that have stable expression of control ShRNA not targeting any gene or ShRNA targeting GnT-III (Mgat3 gene)[3,29]. Flow cytometry data shown in FIG. 4A show that scFvC9 has increased binding to control OVCAR3-PN cells compared with GnT-III ShRNA OVCAR3-PN cells indicating binding specificity for bisecting N-glycans. OVCAR3-PN Control ShRNA and OVACR3-PN GnT-III ShRNA both express periostin protein indicating that the binding is specific to the bisecting N-glycan and not the protein. Next, to evaluate the potential targeting and internalization of scFvC9 we used microscopy to track the binding and distribution of scFvC9 in ovarian cancer cells using the patient-derived cell line OVCA26 previously described[29]. Cell staining of OVCA26 Control ShRNA cells at 5 min indicates an accumulation of scFvC9 at the cell surface (FIG. 4B). The antibody is fully internalized at the 30 min time point. We observed no binding of scFvC9 to OVCA26 GnT-III ShRNA cells further validating the specificity for bisecting N-glycans. We have further evaluated the binding of scFvC9 to glioblastoma cells since this tumor type also has elevated levels of GnT-III expression. Our 30 minute binding data shown in FIG. 4D and FIG. 4E shows that scFvC9 binds to control LN18 cells that display bisecting glycans and there is no binding to LN18 Crispr/Cas9 KO of Mgat3 (FIG. 4E). These data confirm that scFvC9 requires the bisecting glycan for binding and that bisecting structures from other cancers can be targeted. The accumulation of scFvC9 at the cell surface suggests that scFvC9 may be capable of functional in initiating antibody-dependent cell cytotoxicity. The scFvC9 biobody contains a myc tag (FIG. 2) allowing us to expose cells to scFvC9/ anti-myc ab complexes to evaluate cytotoxicity. The ovarian cancer cell line OVCAR5 was premixed with serial dilutions of antibody complexes for 48 hrs before cell viability was measured using a luminescent viability assay. The results indicate that scFvC9 alone or anti-myc ab alone did not induce cytotoxicity (FIG. 4C). However, exposure of the cells to the first two serial dilutions of the complex (2.5 µg/mL and 1.25 µg/mL) had cytotoxic activity.

Targeting, Stability, and Specificity of scFvC9 for Tumors In Vivo

Figure 5:
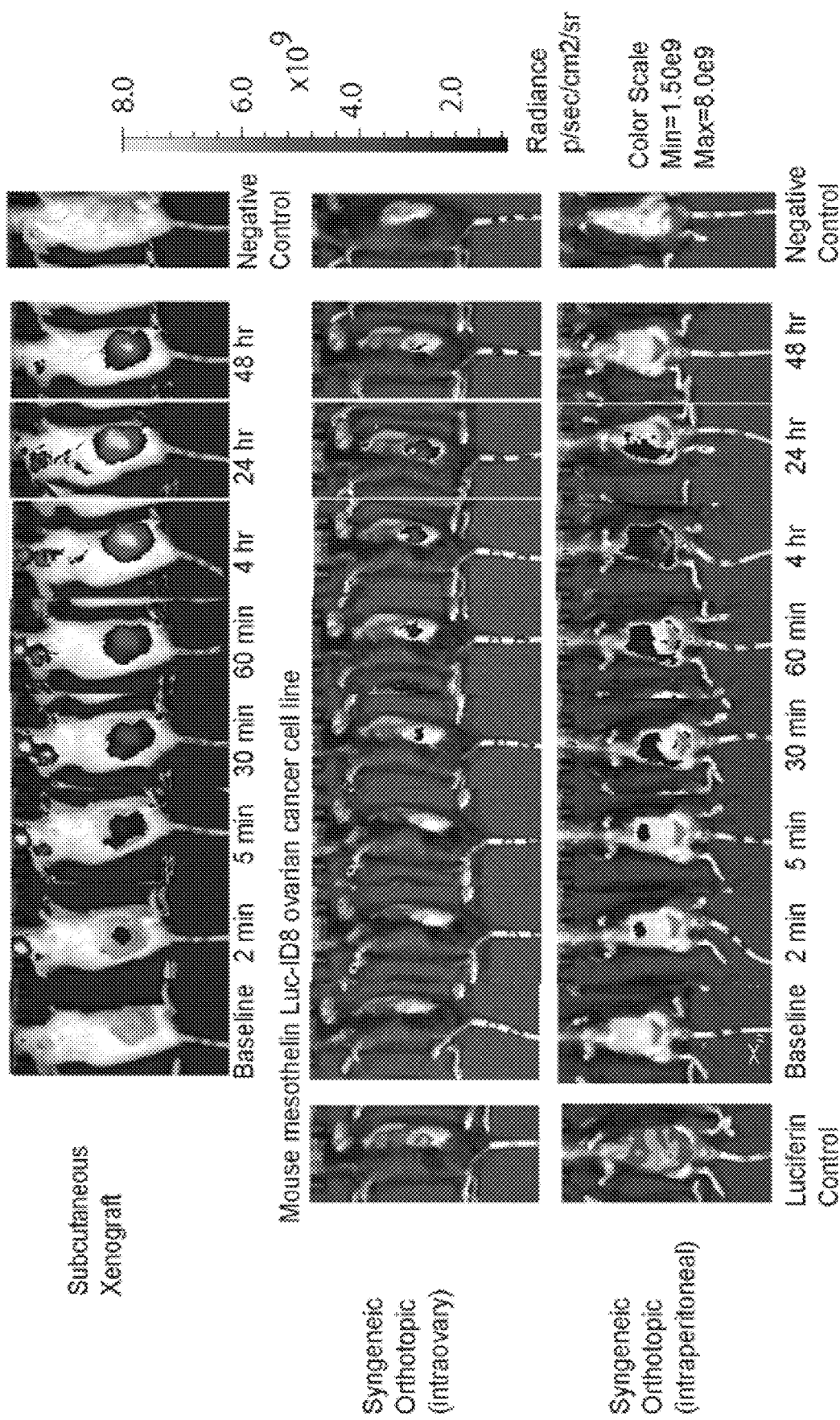
FIG. 5 shows the IVIS imaging of ovarian tumors. Top panel: immune compromised NSG female mice with 6 wk subcutaneous xenograft tumor from A1847 human ovarian cancer cells were imaged before and after retro-orbital injection of scFvC9/IRB680W complexes or negative control (IRB680W only). Middle panel: immune competent C57Bl/6 female mice with 8 wk intraovary Luc-ID8 murine ovarian cancer cells were imaged before and after injection of scFvC9/IRB680W complexes or negative control 9IRB680W only). Lower panel: immune competent C57Bl/6 female mice with 8 wk intraperitoneal Luc-ID8 murine ovarian cancer cells were imaged before and after scFvC9/IRB680W complex injection or IRB680W only.

We used in vivo imaging (IVIS) to evaluate the ability of scFvC9 to target tumors in vivo using both human xenograft and syngeneic mouse models. The top panel of FIG. 5 shows the localization and accumulation of scFvC9 complexed 1:1 with fluorescent-labeled streptavidin in NOD/Scid mice with human A1847 ovarian cancer subcutaneous xenograft tumors established 6 wk prior. The scFvC9 antibody targets the tumor and accumulates in the tumor with a peak at 24 hrs and a gradual decline beginning at 48 hrs. Next, we evaluated the ability of scFvC9 to target luciferase transduced ID8 murine ovarian cancer cells (Luc-ID8) in the immune competent C57Bl/6 female mice. Cells were injected intraovary or intraperitoneal 8 wk prior to IVIS imaging. The scFvC9 antibody complexed 1:1 with fluorescent-labeled streptavidin was injected retro orbitally at the indicated times prior to imaging. The intraovary injections (FIG. 5 middle panel) accumulated at the maximum in the 24 hr time point as observed for the human subcutaneous xenograft injections (FIG. 5, top panel). However, the decline at 48 hr was more substantial. The syngeneic intraperitoneal model reached a maximum accumulation of scFvC9/fluorescent streptavidin complexes at the 4 hr time point. These results confirm that scFvC9 can target both human and mouse ovarian tumors in vivo by retro orbital injection.

To evaluate the specificity of the scFvC9 antibody for tumor tissues and not normal tissues we evaluated antibody localization following injection. NSG mice bearing A1847 subcutaneous tumors were injected with scFvC9 biobody or vehicle only. Mice were sacrificed 24 hr later and tissues were harvested for immunofluorescent staining with streptavidin Qdot 800 to localize the scFvC9 biobody. We observed very punctate signals localized to the periphery of the nuclei in the tumor cells indicative of endosomal compartment localization (FIG. 6 first image lower panel white arrow marks examples). The kidney, an organ known to express non-malignant bisecting N-glycans was negative for the punctate epithelial cell staining of scFvC9 seen in the tumor. While we do observe staining in the blood vessel of the kidney, the epithelial cells of the kidney tissue were negative. Some background staining could be seen in the spleen; but this staining can be observed in areas between nuclei suggesting possible extracellular localization (FIG. 6 third image lower panel arrows show examples) rather than accumulation of the antibody perinuclear as observed with tumor cells (FIG. 4B) and tumor tissue (FIG. 6 first image lower panel). We also notice some accumulation of scFvC9 in the extracellular spaces in the lung. Overall, the scFvC9 antibody demonstrates the ability to preferentially target malignant epithelial cells in vivo via the vasculature.

Magnetic Resonance Imaging (MRI) Validation Studies

Figure 7A:
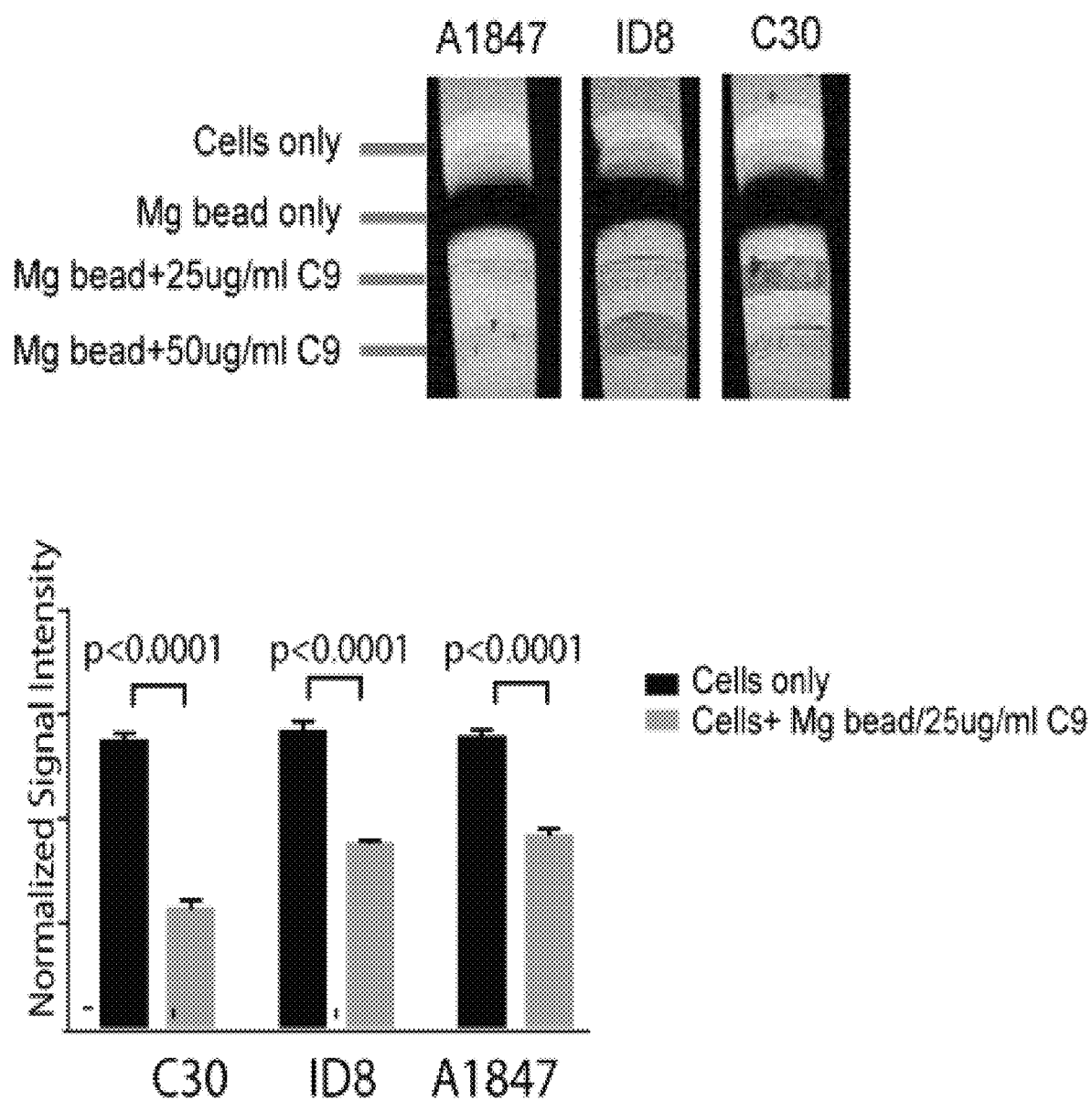

Due to the successful targeting of tumors with scFvC9 we tested whether the scFvC9 biobody could target magnetic beads to the tumor for amplification of signal by magnetic resonance imaging studies. Successful development of scFvC9 as a targeted MR imaging probe would require specificity, magnitude of accumulation, and stability. We started the evaluation of scFvC9 as an MR imaging probe by measuring the ability to detect scFvC9 magnetic bead complexes in ovarian cancer cells in vitro by MRI using phantom tubes. A1847, ID8, and C30 cells were embedded in agarose and layered. Layers of cells only (washed and fixed), anti-flag tag magnetic beads only, or cells (incubated with scFvC9/anti-flag tag magnetic beads prior to wash and fix) were measured using MRI. The results demonstrated a significant reduction of normalized signal intensity was detectable in the layers containing cells with scFvC9/magnetic bead versus cells alone (FIG. 7A). These results illustrate the accumulation of signal amplification.

Next, we initiated subcutaneous A1847 xenograft tumors in NSG mice to test the ability of scFvC9/magnetic bead complexes to target tumors in vivo. Avidin-coated magnetic beads alone or complexed 1:2 with site-specific biotinylated scFv (C9 biobody) were injected IV retro-orbitally. Animals were MR imaged before and at 1 hr, 4 hr, or 24 hr post injection. Regions of interest (ROI) for tumor and control (muscle) were measured across a 2 mm slice. The normalized signal intensity differences between magnetic beads alone and scFvC9/magnetic bead complexes were highly significant at all post injection time points (FIG. 7B). Representative images from the 1 hr post injection time point are shown (FIG. 7B). These data illustrate that scFvC9/ magnetic bead complexes have specificity to target tumor and show signal amplification, specificity, and stability as the reduction in MRI signal for the tumor was consistent from the 1 hr to 24 hr time points.

Discussion

Our results indicate the successful development of an effective screening platform that led to the isolation and purification of a fully human scFv antibody scFvC9 that targets a prominent tumor-specific glycosylation change. We characterized the binding specificity and targeting of this antibody for ovarian cancer and our initial microscopy data using the LN18 glioblastoma cell line indicate that scFvC9 should bind other tumors that exhibit amplification of the Mgat3 gene[23]. We have developed the scFvC9 clone into a biobody allowing large scale purification and demonstrated the specificity of scFvC9 biobody for tumor glycans in vitro and in vivo. The cell surface binding and internalization of the antibody with enhanced stability in vivo are qualities that should enable future development of diverse imaging and therapeutic applications. The scFvC9 biobody could be conjugated to diverse therapeutic molecules such as immune-conjugates, toxins, or drug-conjugates. In addition to these potential therapeutic innovations; the biobody can be useful for tumor imaging and potentially pairing of imaging and therapy options.

Most antibodies developed against tumor antigens target protein despite the fact that there are numerous well-known tumor carbohydrate antigens such as the Tn, sialyl-Tn, Thomsen-Friedenreich (TF), LeX, sialyl-LeX, and LeY[40]. Antibodies that have been isolated to many of these tumor-glycan epitopes are IgM leading to limited applications in clinical use. The isolation of antibodies against membrane protein glycoforms or secreted protein glycoforms from human patient-derived antibody libraries has been limited and this may be due to lower abundance of antibodies that target these antigens within the libraries. Therefore, we employed new strategies in this study to overcome this limitation allowing the isolation of a fully human scFv that targets a prominent tumor-glycan (scFvC9). The repeated subtractions of a patient-derived library with an intact glycoprotein expressing non-tumor glycoforms prior to antigen enrichment using the intact glycoprotein expressing tumor-glycoforms is a key component of our strategy. Our use of mammalian cells to screen the library rather than purified glycoprotein or synthetic synthesized glycopeptides is also unique. To our knowledge, this is the first isolation and description of a human scFv that targets a complex-type N-linked tumor glycan.

Single-chain antibodies have been utilized previously to select for antibodies against glycans. Most of the previously published studies utilized phage-display rather than yeast-display. Yeast antibody libraries display posttranslational modifications similar to mammalian cells and this may offer advantages in solubility and folding. Phage-display was used to isolate human single-chain antibodies toward the glycolipid carbohydrate antigen G(M3) with specificity for melanoma and breast cancer cells in vitro[41]. Another study using phage-display demonstrated that human single-chain antibodies that target sialyl-LeX and LeX could be isolated from a patient-derived library[42]. The most famous tumor carbohydrate antigens, Tn and STn, present a challenge due to the smaller size of these carbohydrate antigens. Single-chain antibodies that target the Tn antigen were isolated due to a strategy that included construction of a mouse scFv library from mice immunized with Jurkat cells that display prominent Tn and STn antigens along with a coordinated subtraction and enrichment strategy led to the isolation of scFv targeting the Tn antigen[43]. Our strategy builds on these studies utilizing the following features: (i) we have screened a patient-derived scFv library developed from the B cells of 11 different ovarian cancer patients (from peripheral blood lymphocytes and ascites) increasing the depth of the library, (ii) we have panned our library using mammalian cells expressing a glycoprotein that displays the tumor-glycans allowing optimal presentation of the tumor glycan, (iii) we utilized multiple rounds of subtraction and enrichment, and (iv) our method uses complementary yeast systems that permit the production of cell surface scFv and secreted scFv with similar conformations minimizing changes in antibody binding specificity.

We are confident that scFvC9 binds tumor-specific bisecting N-glycoforms and is not dependent on periostin protein expression due to our yeast cell-ELISA data, flow cytometry analysis, and cell staining; however, we do not know at this time the exact structures of the N-glycoforms that scFvC9 is binding. The antibody was isolated using a human ovarian cancer cell line that may express differences in the bisecting N-glycoforms from the structures we have previously determined from primary ovarian cancer tissues[3]. Our validation analysis using human ovarian cancer cell lines (OVCA26, C30, A1847), murine ovarian cancer cells (ID8-Luc), and human glioblastoma cells (LN18) that are each distinct from the OVCAR3 cell line that was used to isolate the antibody add confidence that scFvC9 recognizes a broad range of tumor bisecting N-glycans.

There are powerful advantages for antibodies that recognize tumor-glycans. Patients make antibodies against tumor-associated antigens, including glycans. It is known that tumor-specific glycoforms on proteins can overcome immune tolerance[44]. Attempts to elicit humoral immune response to MUC1 peptides failed; yet chemoenzymatically synthesized MUC1 peptide with cancer associated O-glycan Tn and STn epitopes elicited a cancer-specific humoral response[44]. Antibodies that target tumor-glycans may work with checkpoint inhibitors to improve strategies to overcome the immune suppression for solid tumors. Antibodies that target tumor-glycans could improve targeted chemotherapy strategies due to the abundance of the tumor carbohydrate antigen on multiple proteins. Single-chain antibodies to tumor glycans, due to the small size, can be developed into novel therapeutics for glycoproteins that may not have been thought of as traditional drug targets. In summary, our results demonstrate a new approach useful for the isolation of human antibodies that target tumor-specific glycans.

Sequencing of Biobody #C9 (Bb #C9)

We sequenced two clones (E11 and F11) of Biobody #C9. DNA fragments encoding Bb #C9 from E11 and F11 clones were PCR amplified and sequenced. Clones were identical at the protein and DNA level as expected.

The final DNA and protein sequences of biobody #C9 is disclosed in the sequence listing provided herewith. The C9 biobody included a heavy chain with the following heavy chain complementarity-determining regions (CDRs): CDR H1, GFIFDDYAMH (SEQ ID NO: 1), CDR H2, NSGHIDYADSVEGRFT (SEQ ID NO: 2), CDR H3, VSYLSTASSLDY (SEQ ID NO: 3). Surprisingly, the C9 biobody included a truncated light chain with a single light chain CDR-CDR L3, QRYNRAPYT (SEQ ID NO: 4). The sequence of the C9 biobody heavy chain variable region is provided as SEQ ID NO: 5 and the C9 biobody light chain variable region is provided as SEQ ID NO: 6. The protein and DNA sequences of the full-length C9 biobody, including linkers and the V5 tag, are provided as SEQ ID NO: 7 and SEQ ID NO: 8, respectively.

Example 2-In Vivo Imaging Studies

Methods

Model Systems

Figure 8:
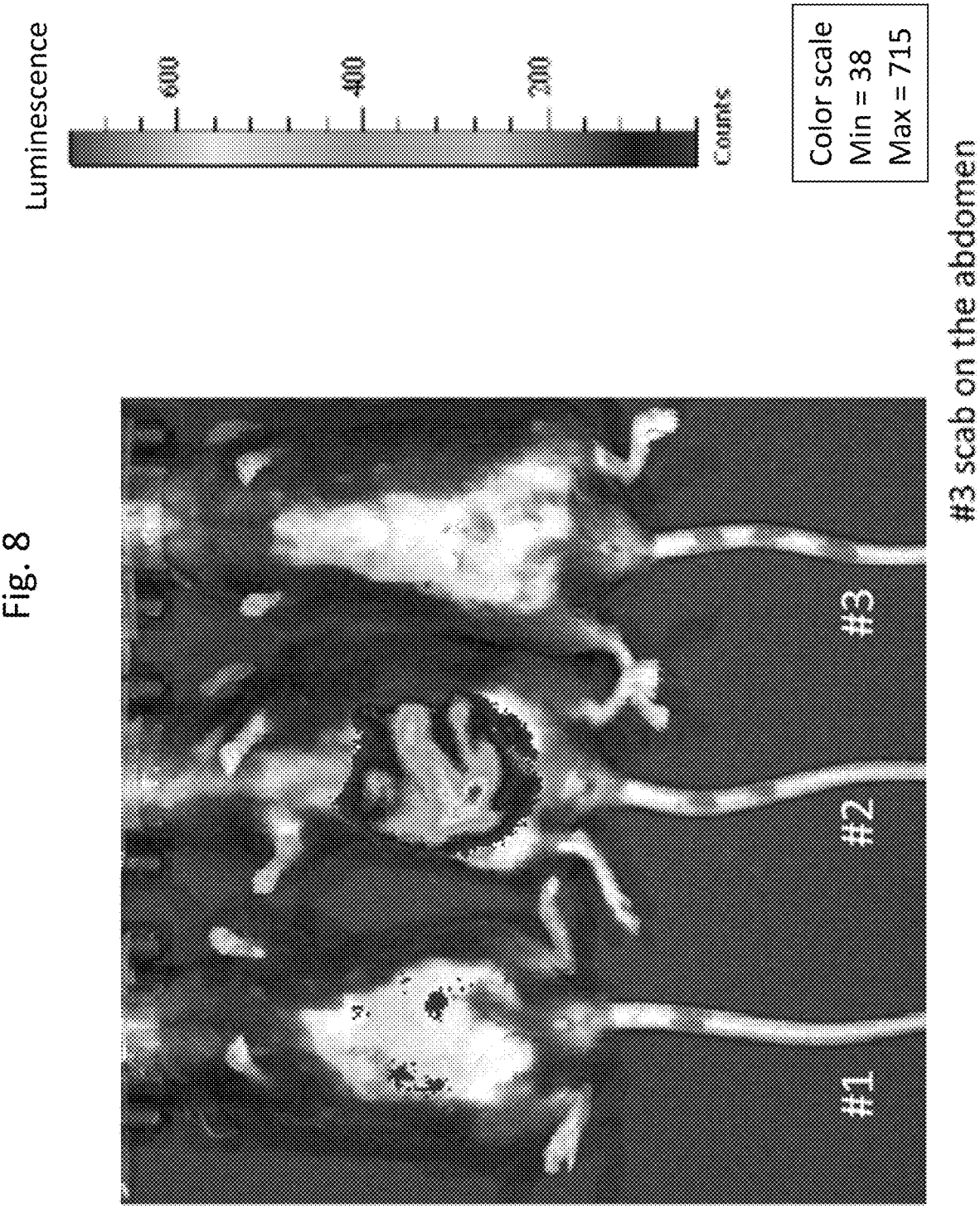
FIG. 8 shows a mouse mesothelin$^{Int}$ Luc-ID8 mouse ovarian cancer model 8 weeks after intraperitoneal injection and in vivo imaging with luciferin.
Figure 9:
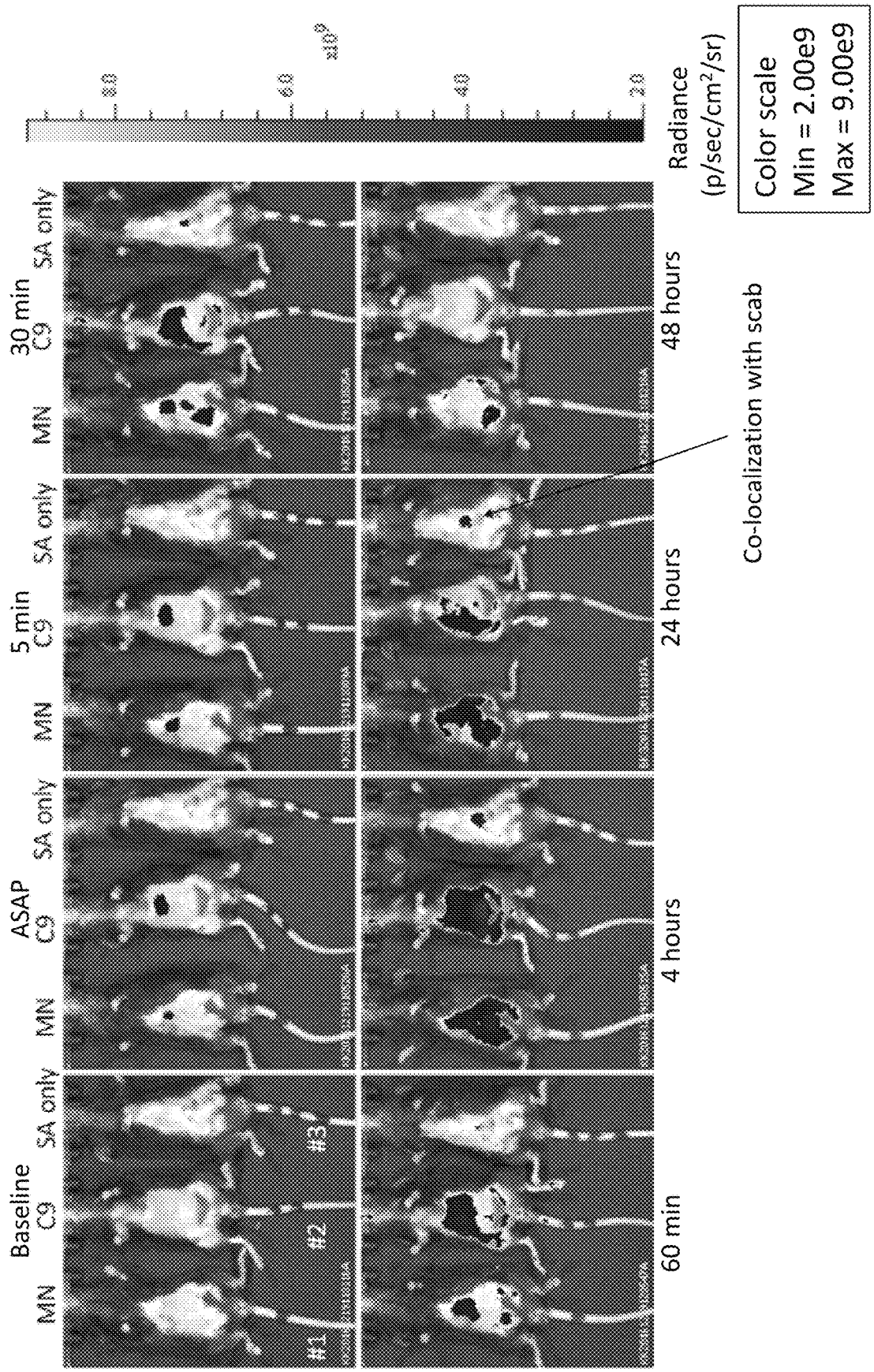
FIG. 9 shows a mouse mesothelin$^{Int}$ Luc-ID8 ovarian cancer in C57Bl/6 female mice (8 weeks after IP injection) and in vivo imaging with a biotinylated anti-mesothelin nanobody (MN) or an anti-N-glycosylated periostin (C9) coupled to labeled streptavidin (SA). Negative control (SA only): C57Bl/6 mouse, injected with labeled streptavidin only.
Figure 10:
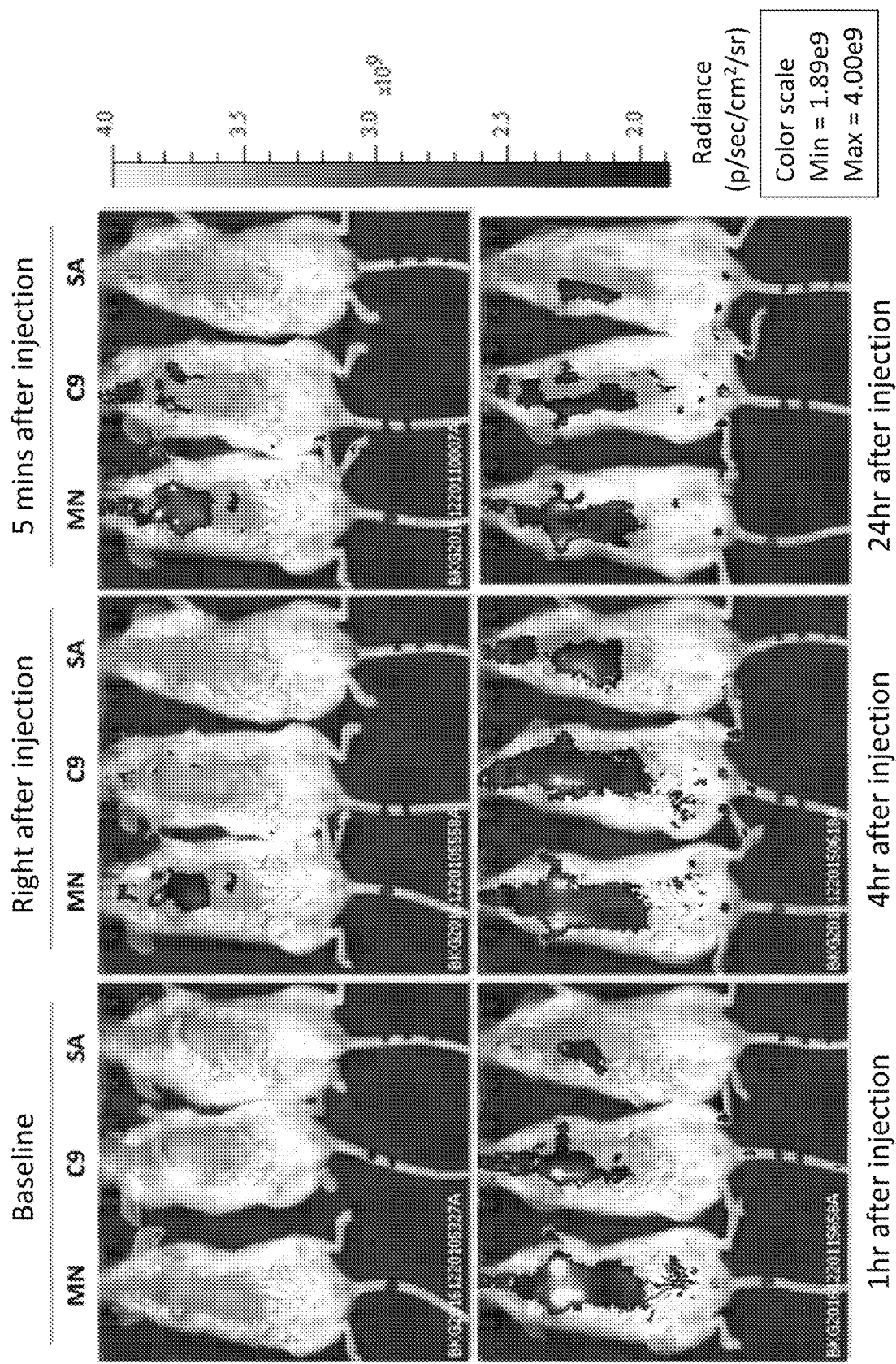
FIG. 10 shows a human mesothelin$^{hi}$ EKVX lung cancer in NSG female mice (4 weeks after IV injection) and in vivo imaging with a biotinylated anti-mesothelin nanobody (MN) or an anti-N-glycosylated periostin (C9) coupled to labeled streptavidin (SA). Negative control (SA): tumor-bearing NSG mouse, injected with labeled streptavidin only.
Figure 10:
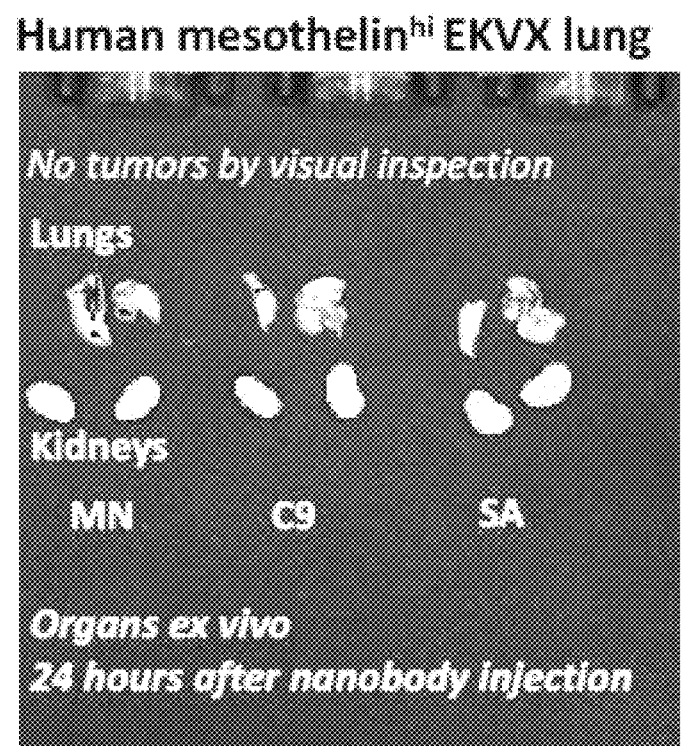
Figure 11:
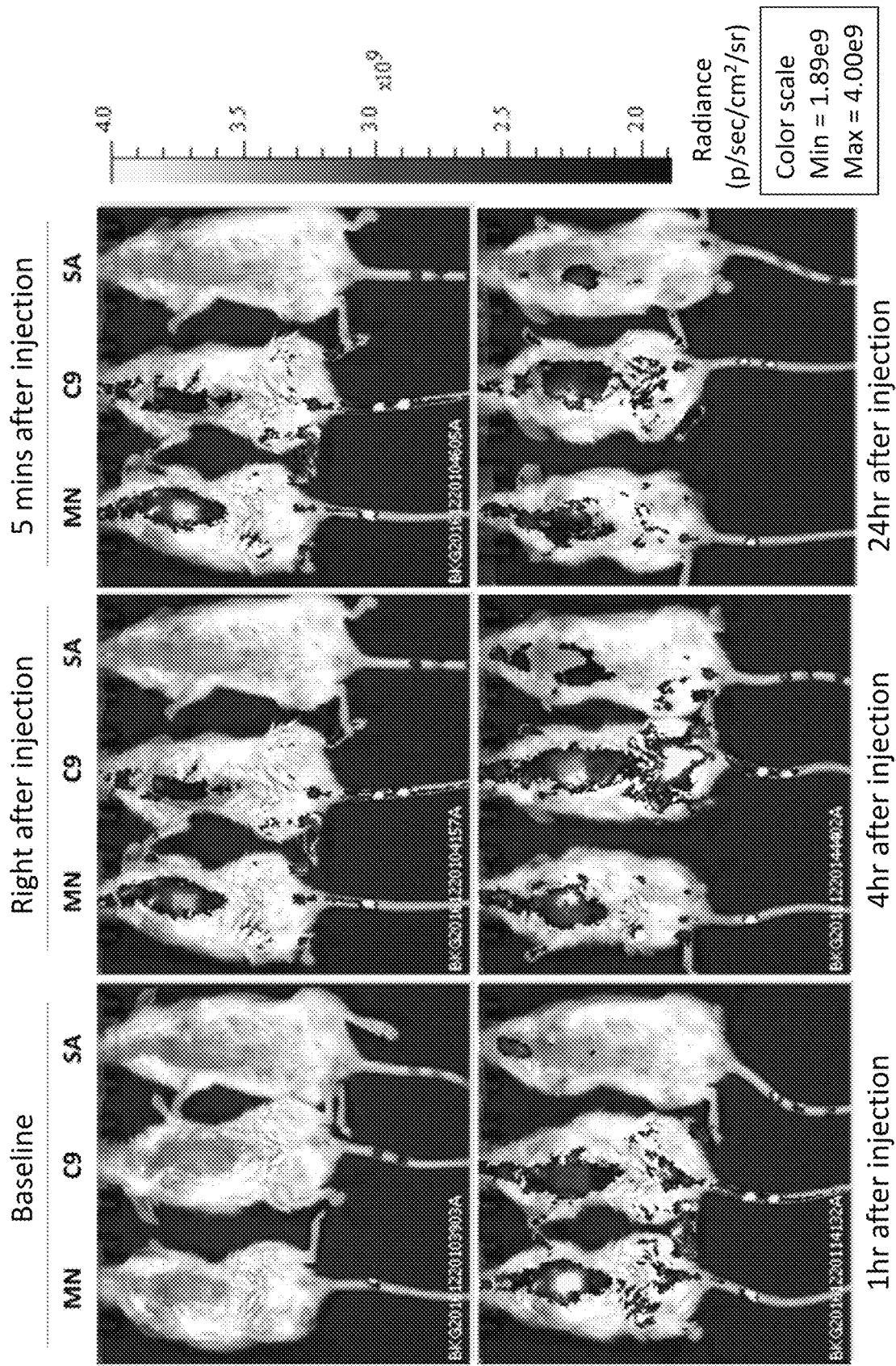
FIG. 11 shows a human mesothelin$^{int}$ H460 lung cancer in NSG female mice (IV injection, 4 weeks) and in vivo imaging with a biotinylated anti-mesothelin nanobody (MN) or an anti-N-glycosylated periostin (C9) coupled to labeled streptavidin (SA). Negative control (SA): tumor-bearing NSG mouse, injected with labeled streptavidin only.
Figure 11:
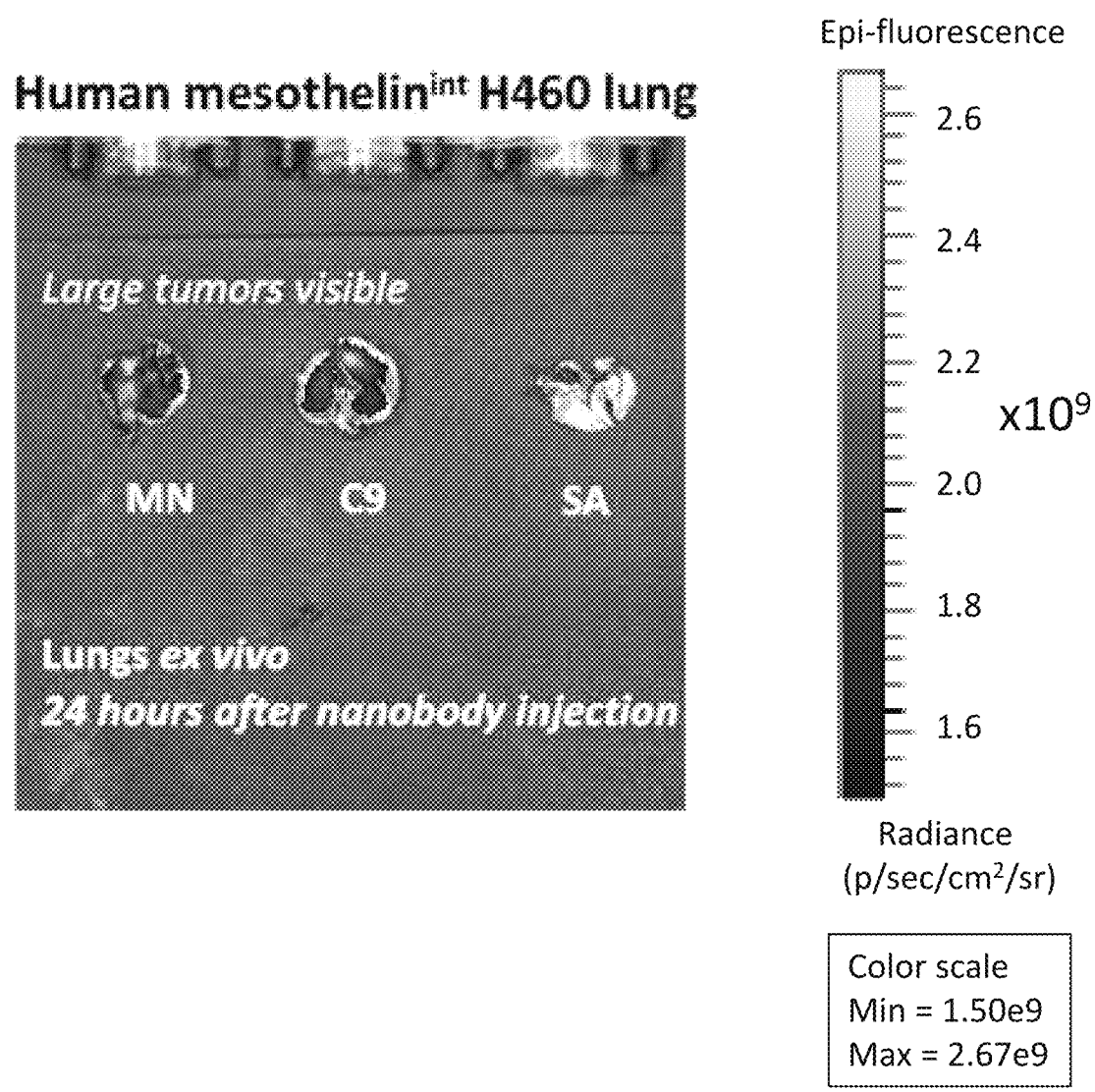
Figure 12:
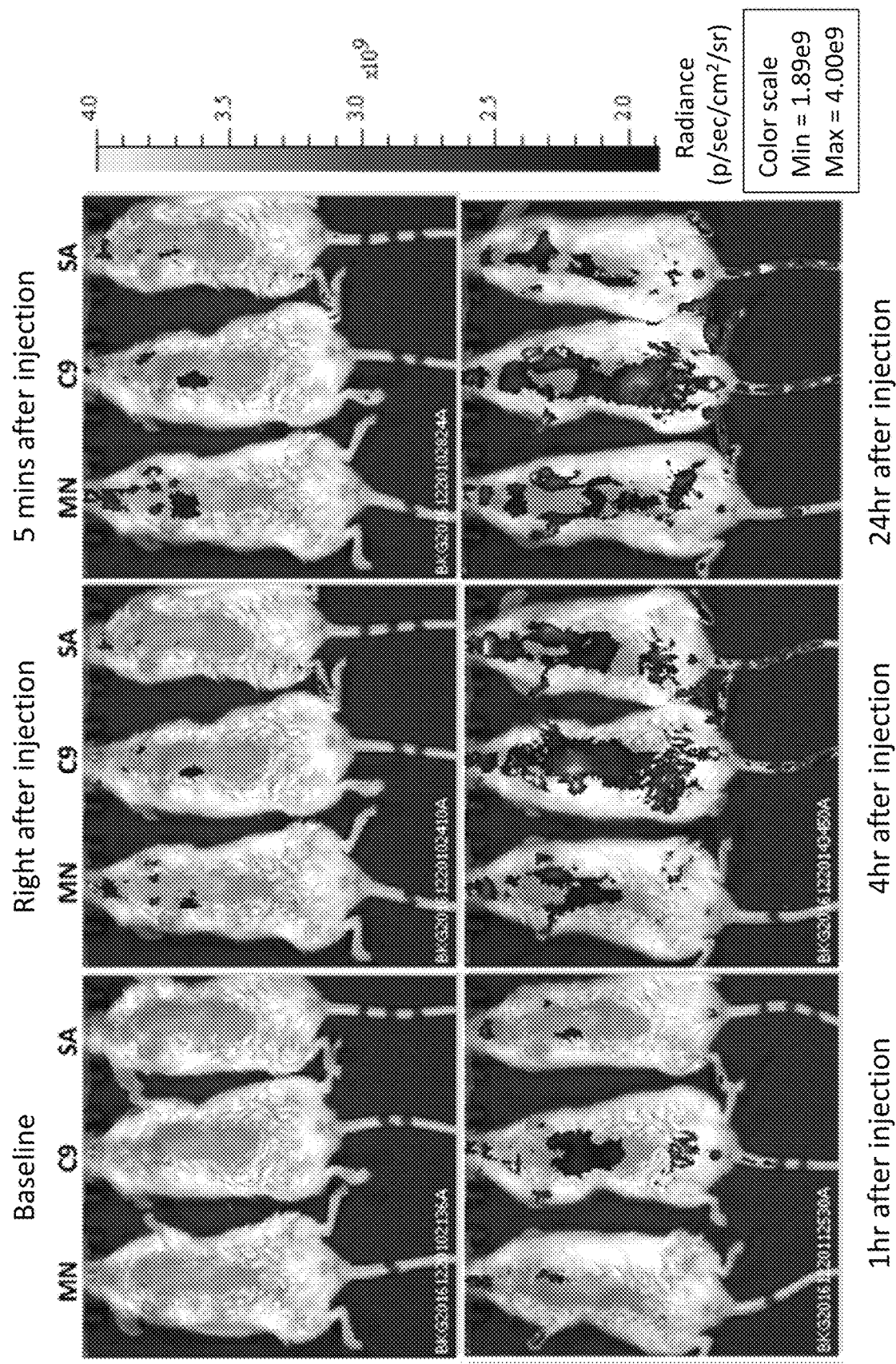
FIG. 12 shows a human mesothelin$^{lo}$ A549 lung cancer in NSG female mice (4 weeks after IV injection) and in vivo imaging with a biotinylated anti-mesothelin nanobody (MN) or an anti-N-glycosylated periostin (C9) coupled to labeled streptavidin (SA). Negative control (SA only): tumor-bearing NSG mouse, injected with labeled streptavidin only.
Figure 12:
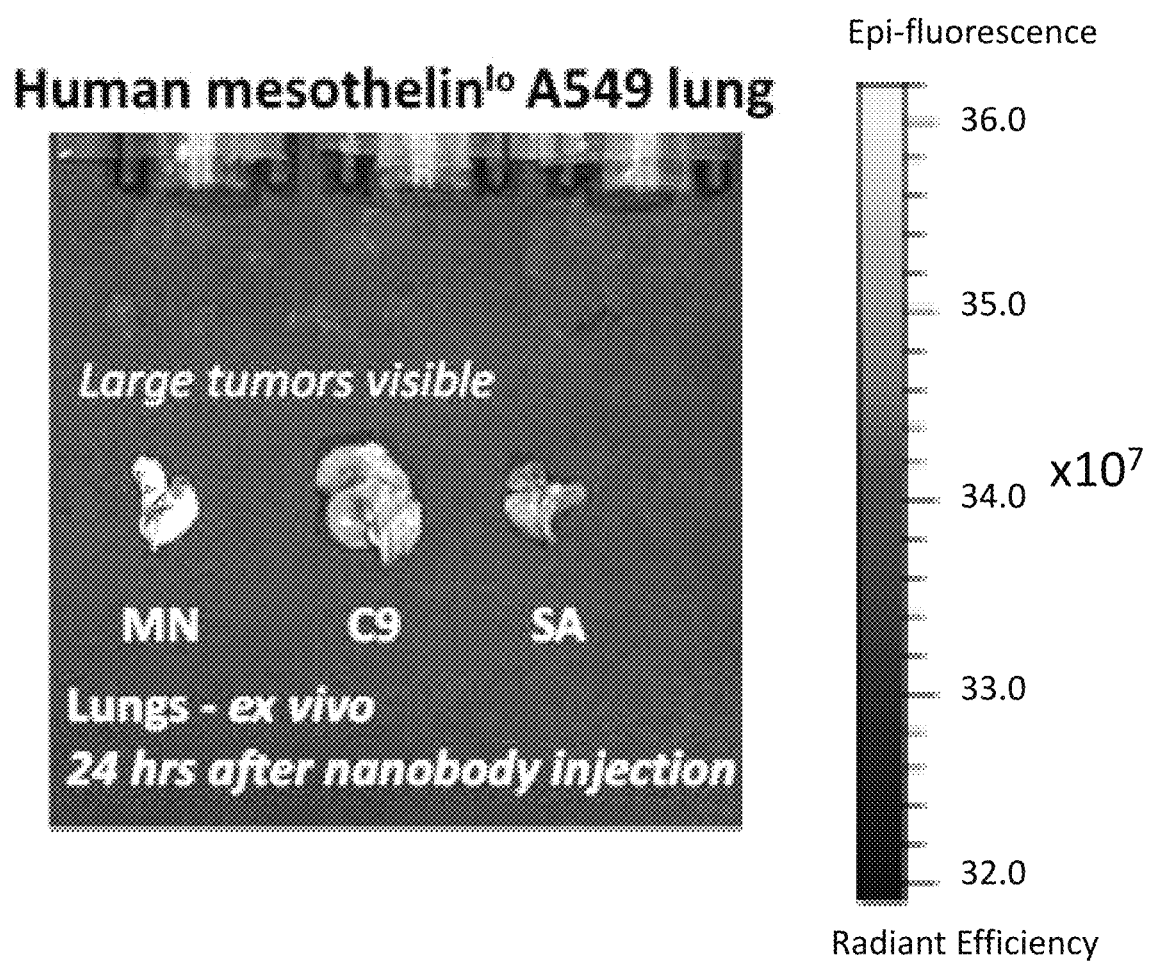

Several lung cancer models were imaged using a labeled anti-mesothelin nanobody (MN) or an anti-N-glycan scFv (C9) antibody. The models included:
  WT C57Bl/6 mice with intra peritoneal mouse mesothelinint Luc-ID8 mouse ovarian cancer (FIGS. 8-9)
  NSG mice with orthotopic human mesothelinlo A549 human lung cancer (FIG. 10)
  NSG mice with orthotopic human mesothelinInt H460 human lung cancer (FIG. 11)
  NSG mice with orthotopic human mesothelinhi EKVX human lung cancer (FIG. 12)

Injections

Retro-ocular injections were performed in the models with 1) biotinylated anti-mesothelin nanobody (MN, 30 μg) coupled to labeled streptavidin IRB680W, 2) biotinylated anti-N-glycan scFv (C9, 30 μg) coupled to labeled streptavidin IRB680W, and 3) labeled streptavidin IRB680W only (negative control).

Image Normalization.

| Luc-ID8 Ortho ovary meso$^{Int}$ | Min: 1.25e9 | Max: 5e9 |
| Luc-ID8 IP ovary meso$^{Int}$ | Min: 2e9 | Max: 9e9 |
| NSG SC ovary meso$^{hi}$ | Min: 1.5e10 | Max: 8e9 |
| NSG SC lung meso$^{hi/Int/lo}$ | Min: 1.89e9 | Max: 4e9 |

Results

The Anti-mesothelin nanobody detected both human and mouse mesothelin expressed by ovary and lung cancers injected intra ovary, IV, IP or SC. Sensitivity was high. Tumors that were barely visualized by luciferin (FIG. 8) or not visible at all (FIG. 10) were detected by the anti-mesothelin nanobody, supporting suitability for cancer early detection. Specificity was high. Large lung tumors that did not express mesothelin were not detected (FIG. 12).

Anti-N-glycan periostine scFv detected both human and mouse ovarian cancers injected intra ovary, IP or SC. C9 biodistribution was faster than mesonano biodistribution, with earlier increase and decrease of signal after injection in all 3 ovarian cancer models tested.

REFERENCES

1 Hakomori, S., Wang, S. M. & Young, W. W., Jr. Isoantigenic expression of Forssman glycolipid in human gastric and colonic mucosa: its possible identity with "A-like antigen" in human cancer. *Proceedings of the National Academy of Sciences of the United States of America* 74, 3023-3027 (1977).
2 Christiansen, M. N. et al. Cell surface protein glycosylation in cancer. *Proteomics* 14, 525-546, doi:10.1002/pmic.201300387 (2014).
3 Allam, H. et al. Glycomic analysis of membrane glycoproteins with bisecting glycosylation from ovarian cancer tissues reveals novel structures and functions. *Journal of proteome research* 14, 434-446, doi:10.1021/pr501174p (2015).
4 Lakshminarayanan, V. et al. Immune recognition of tumor-associated mucin MUC1 is achieved by a fully synthetic aberrantly glycosylated MUC1 tripartite vaccine. *Proceedings of the National Academy of Sciences of the United States of America* 109, 261-266, doi:10.1073/pnas.1115166109 (2012).
5 Boder, E. T. & Wittrup, K. D. Yeast surface display for screening combinatorial polypeptide libraries. *Nature biotechnology* 15, 553-557, doi:10.1038/nbt0697-553 (1997).
6 Scholler, N. Selection of antibody fragments by yeast display. *Methods in molecular biology* 907, 259-280, doi:10.1007/978-1-61779-974-7_15 (2012).
7 Siegel, R. W. Antibody affinity optimization using yeast cell surface display. *Methods in molecular biology* 504, 351-383, doi:10.1007/978-1-60327-569-9_20 (2009).
8 Swers, J. S., Kellogg, B. A. & Wittrup, K. D. Shuffled antibody libraries created by in vivo homologous recombination and yeast surface display. *Nucleic acids research* 32, e36, doi:10.1093/nar/gnh030 (2004).
9 Weaver-Feldhaus, J. M. et al. Yeast mating for combinatorial Fab library generation and surface display. *FEBS letters* 564, 24-34, doi:10.1016/S0014-5793(04)00309-6 (2004).
10 Weaver-Feldhaus, J. M., Miller, K. D., Feldhaus, M. J. & Siegel, R. W. Directed evolution for the development of conformation-specific affinity reagents using yeast display. *Protein engineering, design & selection: PEDS* 18, 527-536, doi:10.1093/protein/gzi060 (2005).
11 Kieke, M. C. et al. Selection of functional T cell receptor mutants from a yeast surface-display library. *Proceedings of the National Academy of Sciences of the United States of America* 96, 5651-5656 (1999).
12 Boder, E. T., Midelfort, K. S. & Wittrup, K. D. Directed evolution of antibody fragments with monovalent femtomolar antigen-binding affinity. *Proceedings of the National Academy of Sciences of the United States of America* 97, 10701-10705, doi:10.1073/pnas.170297297 (2000).
13 Shusta, E. V., Holler, P. D., Kieke, M. C., Kranz, D. M. & Wittrup, K. D. Directed evolution of a stable scaffold for T-cell receptor engineering. *Nature biotechnology* 18, 754-759, doi:10.1038/77325 (2000).
14 Colby, D. W. et al. Potent inhibition of huntingtin aggregation and cytotoxicity by a disulfide bond-free single-domain intracellular antibody. *Proceedings of the National Academy of Sciences of the United States of America* 101, 17616-17621, doi:10.1073/pnas.0408134101 (2004).
15 Colby, D. W. et al. Development of a human light chain variable domain (V(L)) intracellular antibody specific for the amino terminus of huntingtin via yeast surface display. *Journal of molecular biology* 342, 901-912, doi:10.1016/j.jmb.2004.07.054 (2004).
16 Bergan, L., Gross, J. A., Nevin, B., Urban, N. & Scholler, N. Development and in vitro validation of anti-mesothelin biobodies that prevent CA125/Mesothelin-dependent cell attachment. *Cancer letters* 255, 263-274, doi:10.1016/j.canlet.2007.04.012 (2007).
17 Zhao, A. et al. Rapid isolation of high-affinity human antibodies against the tumor vascular marker Endosialin/TEM1, using a paired yeast-display/secretory scFv library platform. *Journal of immunological methods* 363, 221-232, doi:10.1016/j.jim.2010.09.001 (2011).
18 Dangaj, D. et al. Mannose receptor (MR) engagement by mesothelin GPI anchor polarizes tumor-associated macrophages and is blocked by anti-MR human recombinant antibody. *PloS one* 6, e28386, doi:10.1371/journal.pone.0028386 (2011).
19 Li, Y., Siegel, D. L., Scholler, N. & Kaplan, D. E. Validation of glypican-3-specific scFv isolated from paired display/secretory yeast display library. *BMC biotechnology* 12, 23, doi:10.1186/1472-6750-12-23 (2012).
20 Dangaj, D. & Scholler, N. Blocking the B7-H4 pathway with novel recombinant antibodies enhances T cell-mediated antitumor responses. *Oncoimmunology* 2, e25913, doi:10.4161/onci.25913 (2013).
21 Bhaumik, M., Seldin, M. F. & Stanley, P. Cloning and chromosomal mapping of the mouse Mgat3 gene encoding N-acetylglucosaminyltransferase III. *Gene* 164, 295-300 (1995).
22 Abbott, K. L. et al. Focused glycomic analysis of the N-linked glycan biosynthetic pathway in ovarian cancer. *Proteomics* 8, 3210-3220, doi:10.1002/pmic.200800157 (2008).
23 Kohler, R. S. et al. Epigenetic activation of MGAT3 and corresponding bisecting GlcNAc shortens the survival of cancer patients. *Oncotarget* 7, 51674-51686, doi: 10.18632/oncotarget.10543 (2016).
24 Abbott, K. L. et al. Identification of candidate biomarkers with cancer-specific glycosylation in the tissue and serum of endometrioid ovarian cancer patients by glycoproteomic analysis. *Proteomics* 10, 470-481, doi:10.1002/pmic.200900537 (2010).
25 Hortsch, M. & Goodman, C. S. Drosophila fasciclin I, a neural cell adhesion molecule, has a phosphatidylinositol lipid membrane anchor that is developmentally regulated. *The Journal of biological chemistry* 265, 15104-15109 (1990).
26 Tang, Y. et al. Periostin promotes migration and osteogenic differentiation of human periodontal ligament mesenchymal stem cells via the Jun amino-terminal kinases 27. (JNK) pathway under inflammatory conditions. *Cell proliferation*, doi:10.1111/cpr.12369 (2017).
27. Li, W. et al. Periostin: its role in asthma and its potential as a diagnostic or therapeutic target. *Respiratory research* 16, 57, doi:10.1186/s12931-015-0218-2 (2015).
28. Conway, S. J. et al. The role of periostin in tissue remodeling across health and disease. *Cellular and molecular life sciences: CMLS* 71, 1279-1288, doi:10.1007/s00018-013-1494-y (2014).
29. Allam, H. et al. The glycosyltransferase GnT-III activates Notch signaling and drives stem cell expansion to promote the growth and invasion of ovarian cancer. *The Journal of biological chemistry*, doi:10.1074/jbc.M117.783936 (2017).
30. Dangaj, D. et al. Novel recombinant human b7-h4 antibodies overcome tumoral immune escape to potentiate T-cell antitumor responses. *Cancer research* 73, 4820-4829, doi:10.1158/0008-5472.CAN-12-3457 (2013).
31. Dangaj, D. & Scholler, N. Isolation and Validation of Anti-B7-H4 scFvs from an Ovarian Cancer scFv Yeast-Display Library. *Methods in molecular biology* 1319, 37-49, doi:10.1007/978-1-4939-2748-7_2 (2015).
32. Scholler, N., Garvik, B., Quarles, T., Jiang, S. & Urban, N. Method for generation of in vivo biotinylated recombinant antibodies by yeast mating. *Journal of immunological methods* 317, 132-143, doi:10.1016/j.jim.2006.10.003 (2006).
33. Prantner, A. M. et al. Molecular Imaging of Mesothelin-Expressing Ovarian Cancer with a Human and Mouse Cross-Reactive Nanobody. *Molecular pharmaceutics* 15, 1403-1411, doi:10.1021/acs.molpharmaceut.7b00789 (2018).
34. Liu, J. et al. Structural characterizations of human periostin dimerization and cysteinylation. *FEBS letters* 592, 1789-1803, doi:10.1002/1873-3468.13091 (2018).
35. Yun, H., Kim, E. H. & Lee, C. W. (1) H, (13) C, and (15) N resonance assignments of FAS1-IV domain of human periostin, a component of extracellular matrix proteins. *Biomolecular NMR assignments* 12, 95-98, doi:10.1007/s12104-017-9786-z (2018).
36. Chandler, K. B., Leon, D. R., Meyer, R. D., Rahimi, N. & Costello, C. E. Site-Specific N-Glycosylation of Endothelial Cell Receptor Tyrosine Kinase VEGFR-2. *Journal of proteome research* 16, 677-688, doi:10.1021/acs.jproteome.6b00738 (2017).
37. Abbott, K. L. et al. Targeted glycoproteomic identification of biomarkers for human breast carcinoma. *Journal of proteome research* 7, 1470-1480, doi:10.1021/pr700792g (2008).
38. Cummings, R. D. & Kornfeld, S. Characterization of the structural determinants required for the high affinity interaction of asparagine-linked oligosaccharides with immobilized *Phaseolus vulgaris* leukoagglutinating and erythroagglutinating lectins. *The Journal of biological chemistry* 257, 11230-11234 (1982).
39. North, S. J. et al. Glycomics profiling of Chinese hamster ovary cell glycosylation mutants reveals N-glycans of a novel size and complexity. *The Journal of biological chemistry* 285, 5759-5775, doi:10.1074/jbc.M109.068353 (2010).
40. Ragupathi, G. Carbohydrate antigens as targets for active specific immunotherapy. *Cancer immunology, immunotherapy: CII* 43, 152-157 (1996).
41. Lee, K. J. et al. Phage-display selection of a human single-chain fv antibody highly specific for melanoma and breast cancer cells using a chemoenzymatically synthesized G (M3)-carbohydrate antigen. *Journal of the American Chemical Society* 124, 12439-12446 (2002).
42. Mao, S. et al. Phage-display library selection of high-affinity human single-chain antibodies to tumor-associated carbohydrate antigens sialyl Lewisx and Lewisx. *Proceedings of the National Academy of Sciences of the United States of America* 96, 6953-6958 (1999).
43. Kubota, T., Matsushita, T., Niwa, R., Kumagai, I. & Nakamura, K. Novel anti-Tn single-chain Fv-Fc fusion proteins derived from immunized phage library and antibody Fc domain. *Anticancer research* 30, 3397-3405 (2010).
44. Sorensen, A. L. et al. Chemoenzymatically synthesized multimeric Tn/STn MUC1 glycopeptides elicit cancer-specific anti-MUC1 antibody responses and override tolerance. *Glycobiology* 16, 96-107, doi:10.1093/glycob/cwj044 (2006).

The invention claimed is:

1. An antigen-binding reagent comprising a heavy chain variable region comprising SEQ ID NO: 5 and a light chain variable region comprising SEQ ID NO: 6, wherein the antigen-binding reagent specifically binds to a bisecting N-glycan epitope of the human Periostin glycoprotein.

2. The antigen-binding reagent of claim 1, wherein the antigen-binding reagent specifically binds to the bisecting N-glycan epitope of the human Periostin glycoprotein present on cancer cells.

3. The antigen-binding reagent of claim 2, wherein the cancer cells comprise a cancer cell from a cancer selected from the group consisting of ovarian, glioblastoma, kidney, uterine, rectal, colon, adenocarcinoma and lung.

4. The antigen-binding reagent of claim 2, wherein the cancer cells have increased expression of the Mgat3 gene.

5. The antigen-binding reagent of claim 1, wherein the antigen-binding reagent comprises SEQ ID NO: 7.

6. An antigen-binding conjugate comprising the antigen-binding reagent of claim 1 linked to an agent, wherein the agent comprises a detectable imaging agent, a therapeutic agent, or an immunopolypeptide.

7. A cell comprising the antigen-binding reagent of claim 1.

8. A pharmaceutical composition comprising the antigen-binding conjugate of claim 6 and a pharmaceutical carrier.

9. A method for imaging cancer cells in a subject comprising administering in an effective amount the antigen-binding conjugate of claim 6 to the subject, and generating an image of at least a portion of the subject using an imaging modality, wherein the antigen-binding conjugate comprises a detectable imaging agent.

10. The method of claim 9, wherein the imaging of cells bound to the antigen-binding conjugate is indicative of the cells being cancer cells.

11. The method of claim 9, wherein the imaging modality is selected from the group consisting of ultrasound, positron-emission tomography (PET), photon emission computed tomography (SPECT), nuclear magnetic resonance imaging (NMRI), optical imaging (OI) and computed tomography (CT).

12. A method of detecting cancer cells in a subject sample comprising obtaining a sample from the subject, and contacting the sample with the antigen-binding conjugate of claim 6, and detecting binding of the antigen-binding conjugate to cells in the sample.

13. The method of claim 12, wherein the binding of the antigen-binding reagent or the antigen-binding conjugate to the cells is indicative of the cells being cancer cells.

* * * * *